(12) United States Patent
Kodama et al.

(10) Patent No.: US 8,420,568 B2
(45) Date of Patent: Apr. 16, 2013

(54) COLOR-DEVELOPING COMPOSITIONS AND RECORDING MATERIAL CONTAINING SAME

(75) Inventors: Satoshi Kodama, Chiba (JP); Toshiyuki Fukami, Chiba (JP); Hiroshi Fujii, Chiba (JP); Tadashi Kawakami, Chiba (JP); Toshio Aihara, Chiba (JP)

(73) Assignee: Nippon Soda Co., Ltd., Tokyo (JP)

(*) Notice: Subject to any disclaimer, the term of this patent is extended or adjusted under 35 U.S.C. 154(b) by 324 days.

(21) Appl. No.: 12/990,178

(22) PCT Filed: May 1, 2009

(86) PCT No.: PCT/JP2009/001989
§ 371 (c)(1),
(2), (4) Date: Oct. 28, 2010

(87) PCT Pub. No.: WO2009/136491
PCT Pub. Date: Nov. 12, 2009

(65) Prior Publication Data
US 2011/0045973 A1    Feb. 24, 2011

(30) Foreign Application Priority Data

May 7, 2008 (JP) .................. 2008-121604
Aug. 1, 2008 (JP) .................. 2008-199680

(51) Int. Cl.
*B41M 5/333* (2006.01)

(52) U.S. Cl.
USPC ...................... 503/216; 106/31.18

(58) Field of Classification Search .......... None
See application file for complete search history.

(56) References Cited

U.S. PATENT DOCUMENTS 5,801,288 A   9/1998  Fujii et al.
6,037,308 A   3/2000  Sato et al.

FOREIGN PATENT DOCUMENTS

| JP | 08-333329 | 12/1996 |
| JP | 10-029969 | 2/1998 |
| WO | WO 2008/093506 | 8/2008 |

OTHER PUBLICATIONS

International Preliminary Report on Patentability, issued Dec. 13, 2010 during prosecution of International Application PCT/JP2009/001989.

International Search Report, PCT Application No. PCT/JP2009/001989, dated Aug. 4, 2009.

*Primary Examiner* — Bruce H Hess
(74) *Attorney, Agent, or Firm* — Kenyon & Kenyon, LLP

(57) ABSTRACT

Provided is a color-developing composition for recording materials having a superior heat resistance. The color-developing composition is a reaction composition containing a mixture of compounds represented by formula (III) obtained by reacting a dihydroxydiphenylsulfone derivative represented by formula (I) with a dihalide represented by formula (II) X—Y—X (II), wherein, in a composition where the content of a compound with n=1 in said reaction composition is from 5 to 80% by mass of the total solid content of the composition, at least 10% by mass of the compound with n=1 is a crystalline material.

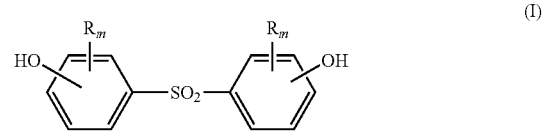

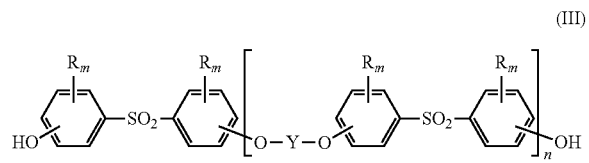

9 Claims, 8 Drawing Sheets

COLOR-DEVELOPING COMPOSITIONS AND RECORDING MATERIAL CONTAINING SAME

TECHNICAL FIELD

The present invention relates to color-developing compositions containing diphenylsulfone cross-linking compounds and to color-developing compositions containing diphenylsulfone cross-linking compounds and having a superior heat resistance.

The present application claims priority to Japanese Patent Application No. 2008-121604 filed on May 7, 2008 and Japanese Patent Application No. 2008-199680 filed on Aug. 1, 2008. Contents of these applications are hereby incorporated by reference in their entirety.

BACKGROUND ART

Diphenylsulfone cross-linking compounds represented by the following formula (IV) are known as a color-developing agent or an image storage stabilizer (e.g., see Patent Document 1).

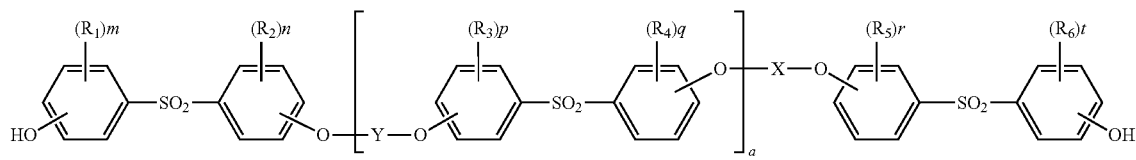

(IV)

[wherein X and Y may each be different from one another, and each either represents a C1-C12 hydrocarbon group which may be linear or branched, saturated or unsaturated and which may have an ether bond, or represents the following formula

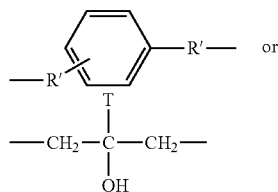

or (wherein R' represents a methylene group or an ethylene group and T represents a hydrogen atom or C1-C4 alkyl group); $R_1$-$R_6$ each independently represents a halogen atom, C1-C6 alkyl group or C2-C4 alkenyl group; m, n, p, q, r and t each represents an integer of 0 to 4 and when representing an integer of 2 or more, $R_1$-$R_6$ may each be different; and "a" represents an integer of 0 to 10]

These compositions, however, had insufficient heat resistance although exerting a remarkably superior storage property compared to the conventional compositions when used for a recording material. Also, as to a mixture of diphenylsulfone cross-linking compounds produced by, for example, reacting 4,4'-dihydroxydiphenylsulfone with bis(2-chloroethyl)ether, it was not easy to remove the raw material 4,4'-dihydroxydiphenylsulfone that remained unreacted.

Since 4,4'-dihydroxydiphenylsulfone referred to above is currently designated as a Type II Monitoring Chemical Substance set forth in the "Law Concerning the Examination and Regulation of Manufacture, etc. of Chemical Substances", it is desired to remove this compound as much as possible.

[Patent Document 1] Japanese Laid-Open Patent Application No. 10-29969

DISCLOSURE OF THE INVENTION

Object to be Solved by the Invention

The object of the present invention is to provide a recording material with a superior heat resistance, and further to provide a color-developing composition with low content of a dihydroxydiphenylsulfone derivative which is a raw material.

Means to Solve the Object

Because a color-developing composition produced by the reaction of 4,4'-dihydroxydiphenylsulfone and bis(2-chloroethyl)ether is a mixture of diphenylsulfone cross-linking compounds with different polymerization degrees, the obtained product after cooling down is amorphous. The present inventors, however, have found that heat resistance at the background part is remarkably improved when a composition, which contains a n=1 compound having an improved crystallinity, is used as a color-developing agent for a recording material. The present inventors have also found that the remaining raw material 4,4'-dihydroxydiphenylsulfone, which had been incorporated in the amorphous composition and could not have been easily removed, can be remarkably reduced by improving the crystallinity of a n=1 compound contained in the composition by causing a reaction of 4,4'-dihydroxydiphenylsulfone and bis 2-chloroethyl)ether, mixing the reaction solution with an organic solvent and then separating the product by filtration, etc. The present invention has thus completed.

Specifically, the present invention relates to: (1) a color-developing composition which is a reaction composition containing a mixture of compounds represented by formula (III)

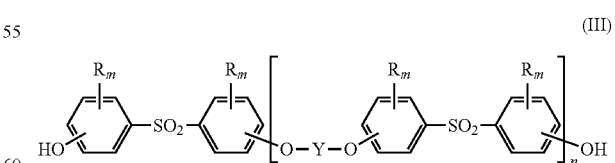

(III)

(wherein R, Y and m have the same meaning as defined below and n represents an integer of 1 to 6) that are obtained by reacting a dihydroxydiphenylsulfone derivative represented by formula (I)

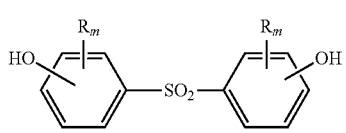

(I)

(wherein each R independently represents a halogen atom, C1-C6 alkyl group or C2-C6 alkenyl group, and m represents an integer of 0 to 4) with a dihalide represented by formula (II)

(II)

{wherein X represents a halogen atom, Y either represents a linear, branched or cyclic C1-C12 hydrocarbon group which may have an ether bond or represents the following formula

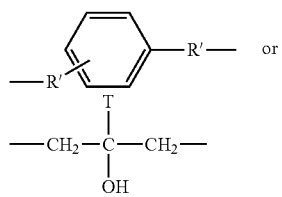

(wherein R' represents a methylene group or ethylene group, and T represents a hydrogen atom or C1-C4 alkyl group)}, wherein the content of a n=1 compound in the reaction composition is 5-80% by mass relative to the solid content in the whole composition and wherein 10% by mass or more of the n=1 compound is a crystalline material; and (2) the color-developing composition according to (1), wherein the compound represented by formula (I) is 4,4'-dihydroxydiphenylsulfone, the dihalide represented by formula (II) is bis(2-chloroethyl)ether, and the n=1 compound of formula (III) which is in an amount of 5-80% by mass relative to the solid content of the whole reaction composition is 2,2'-bis[4-(4-hydroxyphenylsulfonyl)phenoxy]diethylether.

The present invention further relates to: (3) color-developing composition which is a reaction composition of 4,4'-dihydroxydiphenylsulfone and bis(2-chloroethyl)ether, wherein the content of 2,2'-bis[4-(4-hydroxyphenylsulfonyl) phenoxy]diethylether in the reaction composition is 5-80% by mass relative to the solid content in the whole composition and wherein the reaction composition has a peak at 2θ=17.4 in an X-ray diffraction; and (4) the color-developing composition according to (3), which has peaks at 2θ=13.3, 17.4, 18.4 and 21.0 in the X-ray diffraction.

The present invention still further relates to: (5) the color-developing composition according to (1) or (2), wherein the content of the dihydroxydiphenylsulfone derivative represented by formula (I) in the solid content of the reaction composition is 2% by mass or less; and (6) the color-developing composition according to (3) or (4), wherein the content of 4,4'-dihydroxydiphenylsulfone in the solid content of the reaction composition is 2% by mass or less.

The present invention further relates to: (7) a method for producing the color-developing composition according to any one of (1), (2) and (5), wherein the method comprises reacting the dihydroxydiphenylsulfone derivative represented by formula (I) with the dihalide represented by formula (II) in a solvent, mixing the reaction solution with an organic solvent, and separating a product by filtration; (8) a method for producing the color-developing composition according to any one of (3), (4) and (6), wherein the method comprises reacting 4,4'-dihydroxydiphenylsulfone with bis (2-chloroethyl)ether in a solvent, mixing the reaction solution with an organic solvent, and separating a product by filtration; and (9) a recording material comprising the color-developing composition of any one of (1) to (6).

Figure 1:
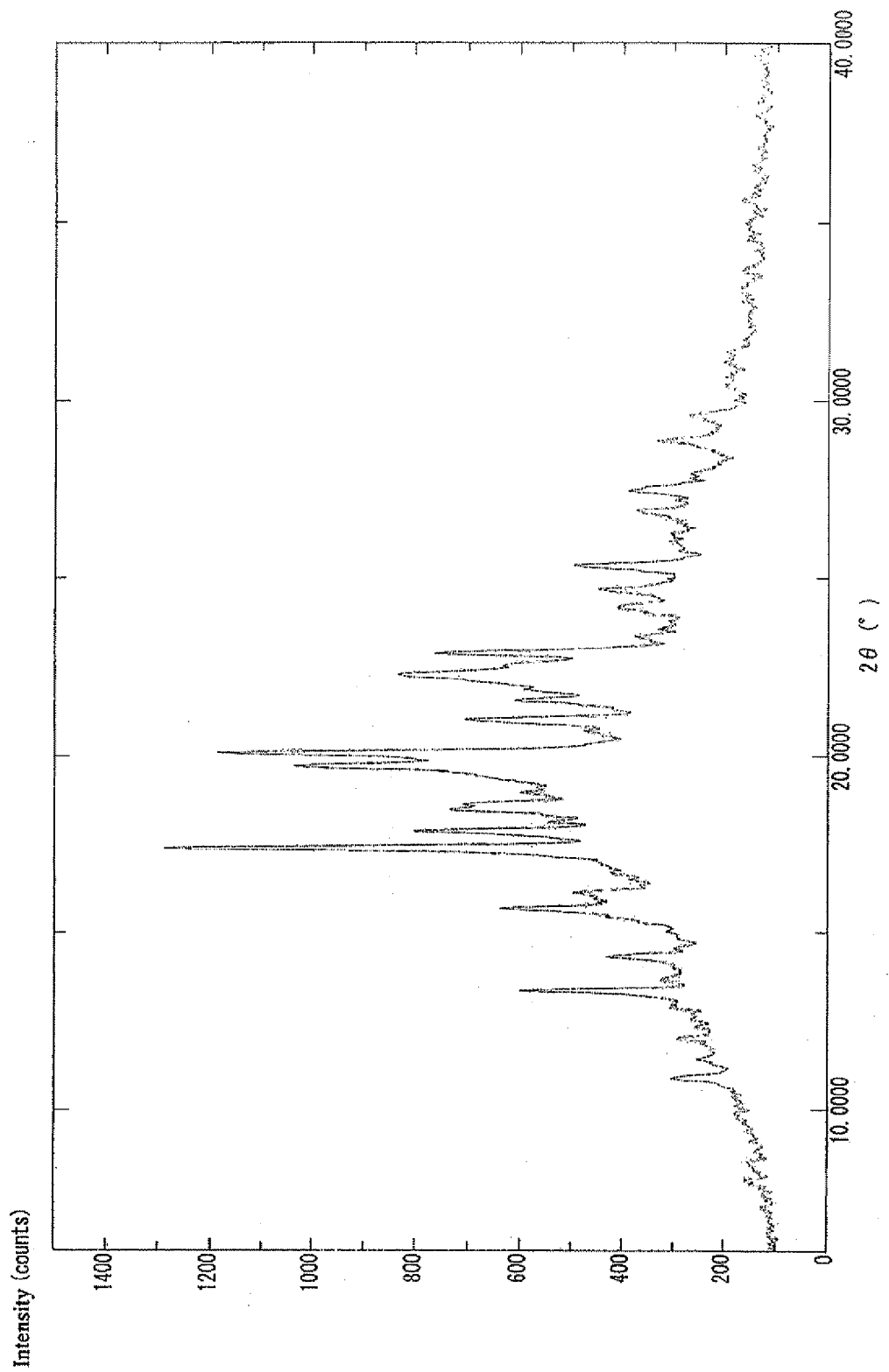
FIG. 1 shows the result of X-ray diffraction carried out for the reaction composition of Example 1 of, the present invention.

MODE OF CARRYING OUT THE INVENTION (Color-developing Composition)

A color-developing composition of the present invention is a reaction composition produced, for example, as follows in a water solvent (e.g. see Japanese Laid-Open Patent Application No. 10-29969 and WO95/33714).

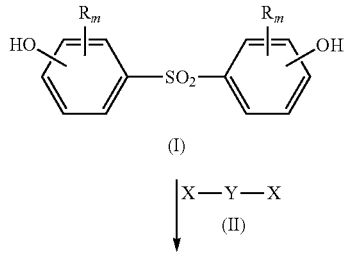

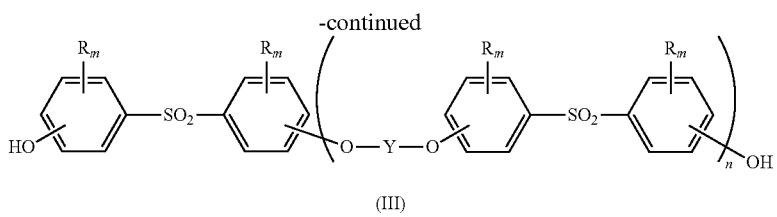

(III)

In the above reaction formula, each R independently represents a halogen atom, C1-C6 alkyl group or C2-C6 alkenyl group. Each Y either represents a linear, branched or cyclic C1-C12 hydrocarbon group which may have an ether bond or represents the following formula

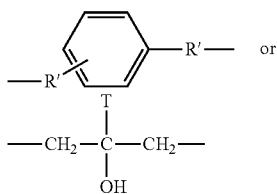

(wherein R' represents a methylene group or an ethylene group, and T represents a hydrogen atom or a C1-C4 alkyl group). X represents a halogen atom. m represents an integer of 0 to 4, and where m is 2 or more, they may be different from each other. n represents an integer of 1 to 6.

Specific examples of the substituent for the compounds represented by the above formulae are shown in the following.

Examples of R include a methyl group, ethyl group, n-propyl group, isopropyl group, n-butyl group, sec-butyl group, tent-butyl group, n-pentyl group, isopentyl group, neopentyl group, tert-pentyl group, n-hexyl group, isohexyl group, 1-methylpentyl group, 2-methylpentyl group, vinyl group, allyl group, isopropenyl group, 1-propenyl group, 2-butenyl group, 3-butenyl group, 1,3-butanedienyl group, and 2-methyl-2-propenyl group.

Examples of X include chlorine, bromine, fluorine and iodine.

Examples of Y include methylene group, ethylene group, trimethylene group, tetramethylene group, pentamethylene group, hexamethylene group, heptamethylene group, octamethylene group, nonamethylene group, decamethylene group, undecamethylene group, dodecamethylene group, methylmethylene group, dimethylmethylene group, methylethylene group, methyleneethylene group, ethylethylene group, 1,2-dimethylethylene group, 1-methyltrimethylene group, 1-methyltetramethylene group, 1,3-dimethyltrimethylene group, 1-ethyl-4-methyl-tetramethylene group, vinylene group, propenylene group, 2-butenylene group, ethynylene group, 2-butynylene group, 1-vinylethylene group, ethyleneoxyethylene group, tetramethyleneoxytetramethylene group, ethyleneoxyethyleneoxyethylene group, ethyleneoxymethyleneoxyethylene group, 1,3-dioxane-5,5-bismethylene group, 1,2-xylyl group, 1,3-xylyl group 1,4-xylyl group, 2-hydroxytrimethylene group, 2-hydroxy-2-methyltrimethylene group, 2-hydroxy-2-ethyltrimethylene group, 2-hydroxy-2-propyltrimethylene group, 2-hydroxy-2-isopropyltrimethylene group and 2-hydroxy-2-butyltrimethylene group. Preferably exemplified is an alkylene group having an ether bond such as an ethyleneoxyethylene group.

A reaction composition is consisting of a mixture of reaction products with different polymerization degrees, and it is preferred that the reaction composition contains all of the compounds from n=1 to n=6 represented by formula (III). However, because the production ratios differ among these compounds depending on reaction conditions and the like, it suffices if only one type of compounds is contained as for the compounds where n is 2 or more. A bis compound where n=1 is essential and is contained by 5-80% by mass, preferably 10-60% by mass, particularly preferably 20-50% by mass relative to the solid content of the reaction composition. The reaction composition is preferably a reaction composition of 4,4'-dihydroxydiphenylsulfone and bis(2-chloroethyl)ether, where the n=1 compound is 2,2'-bis[4-(4-hydroxyphenylsulfonyl)phenoxy]diethylether.

As to a reaction composition of the present invention, 10% by mass or more, preferably 20% by mass or more, more preferably 30% by mass or more and even more preferably 40% by mass or more of a n=1 compound is a crystalline material. Particularly preferred is when 90% by mass or more of a n=1 compound is a crystalline material. In the case of the reaction composition of 4,4'-dihydroxydiphenylsulfone and bis(2-chloroethyl)ether, it means that 10% by mass or more of 2,2'-bis[4-(4-hydroxyphenylsulfonyl)phenoxy]diethylether is a crystalline material. Further, production of a reaction composition by a production method as shown below yields a reaction composition containing the crystalline material of the n=1 compound mentioned above, and at the same time, a reaction composition can be obtained in which the raw material dihydroxydiphenylsulfone derivative represented by formula (I) is contained by 2% by mass or less or even 1% by mass or less relative to the solid content of the reaction composition.

In the present invention, it suffices if the crystalline material of a n=1 compound is contained in a certain amount or more in the reaction composition. Whether the crystalline material is contained in a certain amount or more can be confirmed by using an X-ray diffraction device. For example, in the case of the reaction composition of 4,4'-dihydroxydiphenylsulfone and bis(2-chloroethyl)ether, the crystalline material of 2,2'-bis[4-(4-hydroxyphenylsulfonyl) phenoxy] diethylether which is a n=1 compound has clear peaks at least at $2\theta=13.3, 17.4, 18.4$ and $21.0$, especially at $2\theta=17.4$. The existence of these peaks can be confirmed, because they do not overlap with the peaks of 4,4'-dihydroxydiphenylsulfone and other products having different polymerization degrees. In addition, the ratio of the crystalline material in a n=1 compound can be calculated according to the intensity or area of the peaks.

In the case of a color-developing composition comprising thus obtained reaction composition, specifically in the case of the reaction composition of 4,4'-dihydroxydiphenylsulfone and bis(2-chloroethyl)ether, a recording material with a remarkably superior heat resistance compared to conventional recording materials can be obtained when the recording material is produced using a color-developing composition in which 10% by mass or more of 2,2'-bis[4-(4-hydroxyphenyl-sulfonyl)phenoxy]diethylether is a crystalline material and/or which has a clear peak at 2θ=17.4.

(Method for Producing a Color-developing Composition)

A color-developing composition of the present invention can be obtained by using a reaction composition which was produced in a similar manner to that in Japanese Laid-Open Patent Application No. 10-29969, wherein such reaction composition is adjusted for pH if necessary and mixed with an organic solvent, which mixture is then cooled or allowed to cool and subjected to separation by filtration to obtain a color-developing composition of the present invention. This can be performed either before or after separating the reaction composition from the reaction system by filtration. A color-developing composition of the present invention can be preferably obtained by conducting a reaction in a water solvent, adjusting pH of the reaction solution, adding an organic solvent to the reaction solution, heating the resultant solution which is then cooled or allowed to cool, and then subjecting thus yielded reaction composition to separation by filtration. Further, a color-developing composition of the present invention can also be obtained by separating a reaction composition obtained by a common production method by filtration, subsequently subjecting thus obtained composition to an alkaline treatment in a water solvent again and adjusting for PH, and then mixing the composition with an organic solvent, which is then heated, cooled or allowed to cool, followed by separation by filtration.

An organic solvent to be mixed after the reaction is not particularly limited as long as it is a solvent capable of crystallizing a n=1 compound, while an alcohol solvent and a ketone solvent are preferred. The amount to be added is 5% by mass or more relative to the whole solution.

The alcohol solvent is exemplified by chained or cyclic alcohols such as methanol, ethanol, propanol and isopropanol, where these may be used alone or as a mixed solvent of two or more kinds thereof.

The ketone solvent is exemplified by chained or cyclic ketones such as acetone, methylisobutylketone, cyclopentanone, cyclohexanone and isophorone, where these may be used alone or as a mixed solvent of two or more kinds thereof.

(Recording Material)

When using a color-developing composition of the present invention for thermal recording papers, it may be used in a similar manner to a method of using known image storage stabilizers or color-developing agents. For example, a recording material can be produced as follows. Suspension solutions are mixed and applied onto a support, such as a paper, and dried, wherein the suspension solutions are prepared by respectively dispersing microparticles of a compound of the present invention and microparticles of a color forming compound in the aqueous solutions comprising a water-soluble binder such as polyvinylalcohol and cellulose. Further, apart from the methods as described above wherein the color-developing composition is contained in the color forming layer, the color-developing composition can also be contained in any layer such as a protection layer and undercoating layer when the thermal recording paper comprises a multi-layer structure.

The ratio of a color-developing composition of the present invention to be used relative to a color forming compound is 0.01 to 100 parts by mass relative to 1 part by mass of the color forming compound. When used as a color-developing adjuvant, the ratio is preferably 0.01 to 10 parts by mass and particularly preferably 0.2 to 5 parts by mass relative to 1 part by mass of the color forming compound. When used as a color-developing agent, the ratio is preferably 1 to 10 parts by mass, particularly preferably 1.5 to 5 parts by mass relative to 1 part by mass of the color forming compound.

Two or more kinds of a color-developing composition of the present invention may be used in combination for a recording material of the present invention. For example, among the color-developing compositions of the present invention, one may be used as an image storage stabilizer and another as a color-developing agent, while two or more kinds of the compositions of the present invention may be used in combination as an image storage stabilizer or a color-developing agent. A mixture of the two or more kinds can be prepared by mixing the color-developing compositions in advance or they may be mixed at the point of use. In addition, a color-developing composition may be mixed with a color forming compound or the like in such a manner that the compositions are mixed as powder, or added at the point of the preparation and dispersion of the application solution, or added in the form of a dispersion solution.

Further, n=1 compounds of the present invention includes those having different crystalline forms depending on the conditions for precipitating crystals such as solvent types and the precipitation temperature, or those forming an adduct with the solvent, where all of these belong to the compounds of the present invention. Further, these n=1 compounds can be demonstrated based on the melting point of the crystal, an infrared spectroscopic analysis, X-ray diffraction analysis, etc.

A recording material of the present invention may contain as necessary one or more of the following: another color-developing agent, another image storage stabilizer, sensitizer, loading material, dispersant, antioxidant, desensitizer, anti-adhesive agent, defoamer, light stabilizer, fluorescent brightener, etc. These are respectively used in an amount of usually within a range of 0.01-15 parts by mass, preferably 1-10 parts by mass, relative to 1 part by mass of the color forming compound. These agents may be contained in the color forming layer, while they may be contained in any layer such as a protection layer when the recording material comprises a multi-layer structure. Especially when an overcoating layer or, undercoating layer is provided on the upper part and/or the bottom part of the color forming layer, such overcoating and undercoating layer may contain an antioxidant, light stabilizer, etc. In addition, an antioxidant and a light stabilizer may be contained in these layers in such a manner as being encapsulated in a microcapsule according to need.

Examples of the color forming compound to be used for a recording material of the present invention include: a leuco dye such as fluoran-based, phthalide-based, lactam-based, triphenylmethane-based, phenothiazine-based and spiropyran-based dyes. The color forming compound, however, is not limited to these examples and any color forming compound may be used as long as it develops color by contacting with an acid substance. Further, although it is a matter of course to use these color forming compounds singularly to prepare a recording material of the color developed by the dye used, the color forming compounds may also be used in combination of two or more kinds thereof. For example, it is possible to produce a recording material that develops a real black by using dyes developing three primary colors (red, blue, green) and a black dye in combination.

Examples of the color forming compound include: 3-diethylamino-6-methyl-7-anilinofluoran, 3-di(n-butyl)amino-6-methyl-7-anilinofluoran, 3-(N-methyl-N-cyclohexylamino)-6-methyl-7-anilinofluoran, 3-(N-ethyl-N-isobutylamino)-6-methyl-7-anilinofluoran, 3-(N-methyl-N-propylamino)-6-methyl-7-anilinofluoran, 3-(N-ethyl-N-isoamylamino)-6-methyl-7-anilinofluoran, 3-(N-ethyl-p- toluidino)-6-methyl-7-anilinofluoran, 3-diethylamino-7-(m-trifluoromethylanilino)fluoran, 3-di(n-pentyl)amino-6-methyl-7-anilinofluoran, 3-(N-ethyl-N-ethoxypropylamino)-6-methyl-7-anilinofluoran, 3-diethylamino-6-methyl-7-n-octylaminofluoran, 3-diethylamino-6-methyl-7-(m-methylanilino)fluoran, 3-diethylamino-6-methyl-7-(o,p-dimethylanilino)fluoran, 3-diethylamino-6-chloro-7-anilinofluoran, 3-diethylamino-7-(o-chloroanilino)fluoran, 3-dibutylamino-7-(o-chloroanilino)fluoran, 3-(N-ethyl-N-tetrahydrofurfurylamino)-6-methyl-7-anilinofluran, 3-dibutylamino-7-(o-fluoroanilino)fluoran, 3-diethylamino-7-(o-fluoroanilino)fluoran, 2,4-dimethyl-6-[(4-dimethylamino)anilino]fluoran, 2-chloro-3-methyl-6-p(p-phenylaminophenyl)aminoanilinofluoran, 3,3-bis[1-(4-methoxyphenyl)-1-(4-dimethylaminophenyl)ethylene-2-yl]-4,5,6,7-tetrachlorophthalide, 3,6,6'-tris(dimethylamino)spiro[fluorene-9,3'-phthalide], 3,3-bis(p-dimethylaminophenyl)-6-dimethylaminophthalide, 10-benzoyl-3,7-bis(dimethylamino)phenothiazine, 3-(4-diethylamino-2-hexyloxyphenyl)-3-(1-ethyl-2-methyl-3-indolyl)-4-azaphthalide, 3-(4-diethylamino-2-methylphenyl)-3-(1-ethyl-2-methyl-3-indolyl)-4-azaphthalide, 3-(4-diethylamino-2-ethoxyphenyl)-3-(1-ethyl-2-methyl-3-indolyl)-4-azaphthalide, 3-(4-diethylamino-2-ethoxyphenyl)-3-(1-octyl-2-methyl-3-indolyl)-4-azaphthalide, 3-diethylamino-5-methyl-7-dibenzylaminofluoran, 3-diethylamino-7-dibenzylaminofluoran, 3-(N-ethyl-p-tolyl)amino-7-N-methylanilinofluoran, 3,3-bis(4-diethylamino-2-ethoxyphenyl)-4-azaphthalide, 3-[(2,2-bis(1-ethyl-2-methylindole-3-yl)vinyl]-3-[4-(diethyl amino)phenyl] isobenzofuran-1-one, 3,6,6'-tris(dimethylamino)spiro[fluorene-9,3'-phthalide], 2-[(3,6-bis(diethylamino)-9-(o-chloroanilino)xanthyl]benzoic acid lactam, 3-diethylamlno-7-chlorofluoran, 3,6-bis-(diethylamino)fluoran-γ-(4'-nitro)-anilinolactam, 3-diethylamino-benzo[a]fluoran, 3-(N-ethyl-N-isopentylamino)-benzo[a]fluoran, 2-methyl-6-(N-ethyl-N-p-tolylamino)fluoran, 3,3-bis(1-butyl-2-methyl-3-indolyl)phthalide, 3-diethylamino-6-methyl-7-chlorofluoran, 3-dibutylamino-6-methyl-7-bromofluoran, 3-cyclohexylamino-6-chlorofluoran, 3-diethylamino-6,8-dimethylfluoran, and 4,4'-isopropylidenedi(4-phenoxy)bis[4-(quinazoline-2-yl)-N, N-diethylaniline].

Preferred examples of the black dye include: 3-diethylamino-6-methyl-7-anilinofluoran, 3-di(n-butyl)amino-6-methyl-7-anilinofluoran, 3-(N-methyl-N-cyclohexylamino)-6-methyl-7-anilinofluoran, 3-(N-methyl-N-propylamino)-6-methyl-7-anilinofluoran, 3-(N-ethyl-N-isoamylamino)-6-methyl-7-anilinofluoran, 3-(N-ethyl-p-toluidino)-6-methyl-7-anilinofluoran, 3-diethylamino-7-(m-trifluoromethylanilino)fluoran, 3-di(n-pentyl)amino-6-methyl-7-anilinofluoran, 3-(N-ethyl-N-ethoxypropylamino)-6-methyl-7-anilinofluoran, 3 diethylamino-6-methyl-7-n-octylaminofluoran, 3-diethylamino-6-methyl-7-(m-methylanilino)fluoran, 3-diethylamino-6-chloro-7-anilinofluoran, 3-diethylamino-7-(o-chloroanilino)fluoran, 3-dibutylamino-7-(o-chloroanilino)fluoran, 3-(N-ethyl-N-tetrahydrofurfurylamino)-6-methyl-7-anilinofluoran, and 3-dibutylamino-7-(o-fluoroanilino)fluoran.

Especially preferred examples include: 3-diethylamino-6-methyl-7-anilinofluoran, 3-di(n-butyl)amino-6-methyl-7-anilinofluoran, 3-(N-ethyl-N-isoamylamino)-6-methyl-7-anilinofluoran, 3-(N-ethyl-p-toluidino)-6-methyl-7-anilinofluoran, and 3-di(n-pentyl)amino-6-methyl-7-anilinofluoran.

The near-infrared absorption dye can be exemplified by 3,3-bis[1-(4-methoxyphenyl)-1-(4-dimethylaminophenyl)ethylene-2-yl]-4,5,6,7-tetrachlorophthalide, and 3,6,6'-tris(dimethylamino)spiro[fluorene-9,3'-phthalide].

In addition, examples of the blue dye, green dye, red dye and yellow dye include: 3,3-bis(p-dimethylaminophenyl)-6-dimethylaminophthalide, 3-(4-diethylamino-2-ethoxyphenyl)-3-(1-ethyl-2-methyl-3-indolyl)-4-azaphthalide, 3-(4-diethylamino-2-ethoxyphenyl)-3-(1-octyl-2-methyl-3-indolyl)-4-azaphthalide, 3-diethylamino-7-dibenzylaminofluoran, 3-(N-ethyl-p-tolyl)amino-7-N-methylanilinofluoran, 3,3-bis(4-diethylamino-2-ethoxyphenyl)-4-azaphthalide, 3,6,6'-tris(dimethylamino)spiro[fluorene-9,3'-phthalide], 3-diethylamino-7-chlorofluoran, 3-diethylamino-benzo[a]fluoran, 3-diethylamino-6-methyl-7-chlorofluoran, 3-cyclohexylamino-6-chlorofluoran, 3-diethylamino-6,8-dimethylfluoran, and 4,4'-isopropylidenedi(4-phenoxy)bis[4-(quinazoline-2-yl)-N, N-diethylaniline].

When a color-developing composition of the present invention is used in combination with other color-developing agent, examples of such color-developing agent to be used include the following and they may be used alone or in combination of two or more kinds thereof according to need: a bisphenol compound such as bisphenol A, 4,4'-sec-butylidenebisphenol, 4,4'-cyclohexylidenebisphenol, 2,2'-bis(4-hydroxyphenyl)-3,3'-dimethylbutane, 2,2'-dihydroxydiphenyl, pentamethylene-bis(4-hydroxybenzoate), 2,2'-dimethyl-3,3'-di(4-hydroxyphenyl)pentane, 2,2'-di(4-dihydroxyphenyl)hexane, 2,2-bis(4-hydroxyphenyl)propane, 2,2-bis(4-hydroxyphenyl)butane, 2,2-bis(4-hydroxy-3-methylphenyl)propane, 4,4'-(1-phenylethylidene)bisphenol, 4,4'-ethylidenebisphenol, (hydroxyphenyl)methylphenol, 2,2-bis(4-hydroxyphenyl)-4-methylpentane, 4,4-isopropylidenebis-o-cresol, 4,4'-dihydroxy-diphenylmethane, 2,2'-bis(4-hydroxy-3-phenyl-phenyl)propane, 4,4'-(1,3-phenylenediisopropylidene)bisphenol, 4,4'-(1,4-phenylenediisopropylidene)bisphenol, and 2,2-bis(4-hydroxyphenyl)butyl acetate; a sulfur containing bisphenol such as 4,4'-dihydroxydiphenylthioether, 1,7-di(4-hydroxyphenylthio)-3,5-dioxaheptane, 2,2'-di(4-hydroxyphenylthio)diethylether, 4,4'-dihydroxy-3,3'-dimethylphenylthioether, 1,5-di(4-hydroxyphenylthio)-3-oxapentane, bis(4-hydroxyphenylthioethoxy)methane, and a condensation mixture primarily comprising a binuclear condensate of 2,2'-methylenebis(4-t-butylphenol) described in Japanese Laid-Open Patent Application No. 2003-154760; a 4-hydroxybenzoic acid ester such as 4-hydroxybenzoic acid benzyl, 4-hydroxybenzoic acid ethyl, 4-hydroxybenzoic acid propyl, 4-hydroxybenzoic acid isopropyl, 4-hydroxybenzoic acid butyl, 4-hydroxybenzoic acid isobutyl, 4-hydroxybenzoic acid chlorobenzyl, 4-hydroxybenzoic acid methylbenzyl and 4-hydroxybenzoicaciddiphenylmethyl; a benzoic acid metal salt such as zinc benzoate and zinc 4-nitrobenzoate; a condensate of 4-hydroxybenzoic acid and polyhydric alcohol; salicylic acids such as bis(4-(2-(4-methoxyphenoxy)ethoxy))salicylate, 3,5-bis(α-methylbenzyl)salicylate, and 3,5-bis-tert-butylsalicylate; a salicylate metal salt such as zinc salicylate, and zinc-bis(4-(octyloxycarbonylamino)-2-hydroxybenzoate); hydroxysulfones such as 4,4'-dihydroxy-diphenylsulfone, 4-hydroxy-4'-isopropoxydiphenylsulfone, 4-hydroxy-4'-butoxydiphenylsulfone, 4-hydroxy-4'-phenylsulfonyloxy-3,3'-phenylsulfonyldiphenylsulfone, 4,4'-dihydroxy-3,3'-diallyldiphenylsulfone, 3,4-dihydroxy-4'-methyldiphenylsulfone, 4,4'-dihydroxy-3,3',5,5'-tetrabromodiphenylsulfone, 2-(4-hydroxyphenylsulfonyl)phenol, a mixture of 2-(4-hydroxyphenylsulfonyl)phenol and 4,4'-sulfonyldiphenol, an equivalent mixture of 4-(4-methylphenylsulfonyl)phenol and 2-(4-methylphenylsulfonyl)phenol, 4,4'-sulfonylbis(2-(2-propenyl))phenol, 4-((4-(propoxy)phenyl)sulfonyl)phenol, 4-((4-(allyloxy)phenyl)sulfonyl)phenol, 4-((4-(benzyloxy)phenyl)sulfonyl)phenol, and 2,4-bis(phenylsulfonyl)-5-methyl-phenol; multivalent metal salts such as 4-phenylsulfonylphenoxy zinc, 4-phenylsulfonylphenoxy magnesium, 4-phenylsulfonylphenoxy aluminum and 4-phenylsulfonylphenoxy titanium; 4-hydroxyphthalic acid diesters such as dimethyl 4-hydroxyphthalate; dicyclohexyl 4-hydroxyphthalate, and diphenyl 4-hydroxyphthalate; hydroxy naphthalene acid esters such as 2-hydroxy-6-carboxynaphthalene; hydroxyacetophenone; p-phenylphenol; benzyl 4-hydroxyphenyl acetate; p-benzylphenol; hydroquinone-monobenzylether; trihalomethylsulfones; 4,4'-bis((4-methylphenylsulfonyl)aminocarbonylamino) diphenylmethane; sulfonylureas such as N-(4-methylphenylsulfonyl)-N'-(3-(4-methylphenylsulfonyloxy)phenyl)urea, tetracyanoquinodimethanes; 2,4-dihydroxy-2'-methoxybenzanilide; N-(2-hydroxyphenyl)-2-((4-hydroxyphenyl)thio) acetamide; N-(4-hydroxyphenyl)-2-((4-hydroxyphenyl)thio) acetamide; 4-hydroxybenzenesulfonanilide; 4'-hydroxy-4-methylbenzenesulfonanilide; 4,4'-bis((4-methyl-3-phenoxycarbonyl)aminophenylureide))diphenylsulfone; 3-(3-phenylureide)benzenesulfonamide; octadecyl phosphate; and dodecyl phosphate.

Preferably exemplified are 4,4'-isopropylidenediphenol, 2,2-bis(4-hydroxyphenyl)-4-methylpentane, 4,4'-isopropylidenebis-o-cresol, 4,4'-(1-phenylethylidene)bisphenol, 4,4'-cyclohexylidenebisphenol, 2,2-bis(4-hydroxy-3-phenylphenyl)propane, 4,4'-(1,3-phenylendiisopropylidene) bisphenol, 4,4'-(1,4-phenylendiisopropylidene)bisphenol, bis(p-hydroxyphenyl)butyl acetate, 4,4'-dihydroxydiphenylsulfone, 2,4'-dihydroxydiphenylsulfone, bis(3-allyl-4-hydroxyphenyl)sulfone, 4-hydroxy-4'-isopropoxydiphenylsulfone, 4-hydroxy-4'-n-propoxydiphenylsulfone, 4-hydroxy-4'-allyloxydiphenylsulfone, 4-hydroxy-4'-benzyloxydiphenylsulfone, 3,4-dihydroxyphenyl-4'-methylphenylsulfone, N-(2-hydroxyphenyl)-2-[(4-hydroxyphenyl)thio]acetamide, N-(4-hydroxyphenyl)-2-[(4-hydroxyphenyl)thio]acetamide, an equivalent mixture of N-(2-hydroxyphenyl)-2-[(4-hydroxyphenyl)thio]acetamide and N-(4-hydroxyphenyl)-2-[(4-hydroxyphenyl)thio]acetamide, benzyl p-hydroxybenzoate, di(4-hydroxy-3-methylphenyl)sulfide, 4-hydroxybenzene sulfonanilide, hydroquinonemonobenzyl ether, a condensation mixture primarily comprising a binuclear condensate of 2,2'-methylenebis(4-t-butylphenol) described in Japanese Laid-Open Patent Application No. 2003-154760, 4,4'-bis(N-p-tolylsulfonylaminocarbonylamino)diphenylmethane, N-p-tolylsulfonyl-N'-3-(p-tolylsulfonyloxy)phenylurea, 4,4'-bis[(4-methyl-3-phenoxycarbonylaminophenylureide)]diphenylsulfone, 3-(3-phenylureide)benzenesulfonamide, zinc-bis[4-(n-octyloxycarbonylamino)salicylate]dihydrate, zinc 4-[(2-(4-methoxyphenoxy)ethoxy]salicylate, and zinc 3,5-bis(α-methylbenzyl)salicylate.

More specifically, these color-developing agents may be appropriately used at a ratio of such as 0.1 to 10 parts by mass relative to 1 part by mass of a color-developing composition of the present invention. For example, a thermal recording paper can be produced by combining 1 part by mass of a color-developing composition of the present invention and 1 part by mass of 4-hydroxy-4'-isopropoxydiphenylsulfone as other color-developing agent, relative to 1 part by mass of 3-di(n-butyl)amino-6-methyl-7-anilinofluoran as a dye. Likewise, the color-developing agents referred to above such as 4-hydroxy-4'-n-propoxydiphenylsulfone, 4-hydroxy-4'-allyloxydiphenylsulfone, and 2,4'-dihydroxydiphenylsulfone may be combined.

When a color-developing composition of the present invention is used, in combination with other image storage, stabilizer, the examples of such image storage stabilizer include the following and they may be used alone or in combination of two or more kinds thereof according to need: 1,1,3-tris(2-methyl-4-hydroxy-5-t-butylphenyl)butane, 1,1,3-tris(2-methyl-4-hydroxy-5-t-cyclohexylphenyl)butane, 4,4'-butylidenebis(6-t-butyl-3-methylphenol), 2,2'-methylenebis(6-t-butyl-4-methylphenol), 2,2'-methylenebis(6-t-butyl-4-ethylphenol), 4,4'-thiobis(6-t-butyl-3-methylphenol), 1,3,5-tris(2,6-dimethyl-4-t-butyl-3-hydroxybenzyl)isocyanurate, 1,3,5-tris[[3,5-bis(1,1-dimethylethyl)-4-hydroxyphenyl]meth yl]-1,3,5-triazine-2,4,6(1H,3H,5H)-trione, 2-methyl-2-([4-[[4-(phenylmethoxy)phenyl]sulfonyl] phenoxy]methyl]-oxirane, 2,4,8,10-(tetra(t-butyl)-6-hydroxy-12H-dibenzo[d,g][1,3,2]dioxaphosphocin-6-oxide sodium salt, 2,2-bis(4'-hydroxy-3',5'-dibromophenyl)propane, 4,4'-sulfonylbis(2,6-dibromophenol) 2-(2'-hydroxy-5'-methylphenyl)benzotriazole, 4-benzyloxy-4-(2-methylglycidyloxy)-diphenylsulfone, 4,4'-diglycidyloxydiphenylsulfone, 1,4-diglycidyloxybenzene, 4-(α-(hydroxymethyl)benzyloxy)-4'-hydroxydiphenylsulfone, and 2,2-methylenebis(4,6-tert-butylphenyl)phosphate.

Preferably exemplified are 1,1,3-tris(2-methyl-4-hydroxy-5-t-butylphenyl)butane, 1,1,3-tris(2-methyl-4-hydroxy-5-t-cyclohexylphenyl)butane, 4,4'-butylidenebis(6-t-butyl-3-methylphenol), 2,2'-methylenebis(4-ethyl-6-t-butylphenol), 1,3,5-tris(2,6-dimethyl-4-t-butyl-3-hydroxybenzyl) isocyanurate, 2-methyl-2-[[4-[[4-(phenylmethoxy)phenyl]sulfonyl]phenoxy]methyl]-oxirane, 4,4'-sulfonylbis(2,6-dibromophenol), and 2-(2'-hydroxy-5'-methylphenyl) benzotriazole.

Examples of the sensitizer include the following and they may be used alone or in combination of two or more kinds thereof according to need: a higher fatty acid amide such as stearic acid amide; benzamide; stearic acid anilide; acetoacetanilide; thioacetanilide; dibenzyl oxalate; di(4-methylbenzyl)oxalate; di(4-chlorobenzyl)oxalate; dimethyl phthalate; dimethyl terephthalate; dibenzyl terephthalate; dibenzyl isophthalate; bis(tert-butylphenol); diphenylsulfone and its derivative such as 4,4'-dimethoxydiphenylsulfone, 4,4'-diethoxydiphenylsulfone, 4,4'-dipropoxydiphenylsulfone, 4,4'-diisopropoxydiphenylsulfone, 4,4'-dibutoxydiphenylsulfone, 4,4'-diisobutoxydiphenylsulfone, 4,4'-dipentyloxydiphenylsulfone, 4,4'-dihexyloxydiphenylsulfone, 2,4'-dimethoxydiphenylsulfone, 2,4'-diethoxydiphenylsulfone, 2,4'-dipropoxydiphenylsulfone, 2,4'-diisopropoxydiphenylsulfone, 2,4'-dibutoxydiphenylsulfone, 2,4'-dipentyloxydiphenylsulfone, 2,4'-dihexyloxydiphenylsulfone; diethers of 4,4'-dihydroxydiphenylsulfone; diethers of 2,4'-dihydroxydiphenylsulfone; 1,2-bis(phenoxy)ethane; 1,2-bis(4-methylphenoxy)ethane; 1,2-bis(3-methylphenoxy)ethane; diphenylamine; carbazole; 2,3-di-m-tolylbutane; 4-benzylbiphenyl; 4,4'-dimethylbiphenyl; m-terphenyl; di-p-naphthylphenylenediamine; 1-hydroxy-2-naphthoic acid phenyl ester; 2-naphthylbenzyl ether; 4-methylphenyl-biphenylether; 1,2-bis(3,4-dimethylphenyl) ethane; 2,3,5,6-tetramethyl-4'-methyldiphenylmethane; 1,2-bis(phenoxymethyl)benzene; acrylic acid amide; diphenylsulfone; 4-acetylbiphenyl; and carbonic acid diphenyl.

Preferably exemplified are 2-naphthylbenzylether, m-terphenyl, p-benzylbiphenyl, benzyl oxalate, di(p-chlorobenzyl)oxalate, an equivalent mixture of benzyl oxalate and di(p-chlorobenzyl)oxalate, di(p-methylbenzyl)oxalate, an equivalent mixture of di(p-chlorobenzyl) oxalate and di(p-methylbenzyl)oxalate, 1-hydroxy-2-naphthoic acid phenyl ester, 1,2-diphenoxyethane, 1,2-di-(3-methylphenoxy) ethane, 1,2-bis(phenoxymethyl)benzene, dimethyl terephthalate, stearic acid amide, "amide AP-1" (a mixture of stearic acid amide and palmitic acid amide at 7:3), diphenylsulfone, and 4-acetylbiphenyl.

More specifically, these sensitizers may be appropriately used at a ratio of 0.1 to 10 parts by mass relative to 1 part by mass of a dye. For example, a thermal recording paper can be produced by combining 2 parts by mass of a color-developing composition of the present invention and 1 part by mass of di(p-methylbenzyl)oxalate as a sensitizer, relative to 1 part by mass of 3-di(n-butyl)amino-6-methyl-7-anilinofluoran as a dye. Likewise, the sensitizers referred to above such as 1,2-di-(3-methylphenoxy)ethane, 1,2-bis(phenoxymethyl)benzene and diphenylsulfone may be combined.

As a loading material, the followings can be used: silica, clay, kaolin, fired kaolin, talc, satin white, aluminum hydroxide, calcium carbonate, magnesium carbonate, zinc oxide, titanium oxide, barium sulfate, magnesium silicate, aluminum silicate, plastic pigment, etc. Particularly preferred for a recording material of the present invention is a salt of alkaline earth metal. A carbonate salt is further preferred, and calcium carbonate, magnesium carbonate, etc. are preferable. The ratio of loading material for use is 0.1 to 15 parts by weight, preferably 1 to 10 parts by weight relative to 1 part by weight of the color forming compound. In addition, the loading materials referred to above can be mixed for use.

Examples of the dispersant include sulfosuccinic acid esters such as dioctyl sodium sulfosuccinate, dodecylbenzenesulfonic acid sodium, sodium salt of lauryl alcohol sulfate ester, and a fatty acid salt.

Examples of the antioxidant include 2,2'-methylenebis(4-methyl-6-tert-butylphenol), 2,2'-methylenebis(4-ethyl-6-tert-butylphenol), 4,4"-propylmethylenebis(3-methyl-6-tert-butylphenol), 4,4'-butylidenebis(3-methyl-6-tert-butylphenol), 4,4'-thiobis(2-tert-butyl-5-methylphenol), 1,1,3-tris(2-methyl-4-hydroxy-5-tert-butylphenol)butane, 4-[4-{1,1-bis(4-hydroxyphenyl)ethyl}-α, α'-dimethylbenzyl] phenol, 1,1,3-tris(2-methyl-4-hydroxy-5-cyclohexylphenyl) butane, 2,2'-methylenebis(6-tent-butyl-4-methylphenol), 2,2'-methylenebis(6-tert-butyl-4-ethylphenol), 4,4'-thiobis (6-tert-butyl-3-methyl-phenol, 1,3,5-tris((4-(1,1-dimethylethyl)-3-hydroxy-2,6-dimethylphe nyl)methyl-1,3,5-triazine-2,4,6(1H,3H,5H)-trione, and 1,3,5-tris((3,5-bis(1,1-dimethylethyl)-4-hydroxyphenyl)meth yl)-1,3,5-triazine-2, 4,6(1H,3H,5H)-trione.

The desensitizer is exemplified by a fatty higher alcohol, polyethyleneglycol and guanidine derivative.

The antiadhesive agent is exemplified by stearic acid, zinc stearate, calcium stearate carnauba wax, paraffin wax and ester wax.

Examples of the light stabilizer include: a salicylic acid-based ultraviolet absorber such as phenylsalicylate, p-tert-butylphenylsalicylate, and p-octylphenylsalicylate; a benzophenone-based ultraviolet absorber such as 2,4-dihydroxybenzophenone, 2-hydroxy-4-methoxybenzophenone, 2-hydroxy-4-benzyloxybenzophenone, 2-hydroxy-4-dodecyloxybenzophenone, 2,2'-dihydroxy-4-methoxybenzophenone, 2,2'-dihydroxy-4,4'-dimethoxybenzophenone, 2-hydroxy-4-methoxy-5-sulfobenzophenone, and bis(2-methoxy-4-hydroxy-5-benzoylphenyl)methane; a benzotriazole-based ultraviolet absorber such as 2-(2'-hydroxy-5'-methylphenyl)benzotriazole, 2-(2'-hydroxy-5'-tert-butylphenyl)benzotriazole, 2-(2'-hydroxy-3',5'-di-tert-butylphenyl)benzotriazole, 2-(2'-hydroxy-3-tert-butyl-5'-methylphenyl)-5-chlorobenzotriazole, 2-(2'-hydroxy-3',5'-di-tert-amylphenyl) benzotriazole, 2-(2'-hydroxy-3',5'-di-test-butylphenyl)-5-chlorobenzotriazole, 2-(2'-hydroxy-5'-tert-butylphenyl) benzotriazole, 2-(2'-hydroxy-5'-(1",1",3",3"-tetramethylbutyl)phenyl)benzotriazole, 2-[2'-hydroxy-3'-(3",4",5",6"-tetrahydrophthalimidomethyl)-5'-methylphenyl]benzotriazole, 2-(2'-hydroxy-5'-tent-octylphenyl)benzotriazole, 2-(2'-hydroxy-3',5'-bis(α,α'-dimethylbenzyl)phenyl)-2H-benzotriazole, 2-(2'-hydroxy-3'-dodecyl-5'-methylphenyl)benzotriazole, 2-(2'-hydroxy-3'-undecyl-5'-methylphenyl)benzotriazole, 2-(2'-hydroxy-3'-tridecyl-5'-methylphenyl)benzotriazole, 2-(2'-hydroxy-3'-tetradecyl-5'-methylphenyl)benzotriazole, 2-(2'-hydroxy-3'-pentadecyl-5'-methylphenyl)benzotriazole, 2-(2'-hydroxy-3'-hexadecyl-5'-methylphenyl)benzotriazole, 2-[2'-hydroxy-4'-(2"-ethylhexyl)oxyphenyl]benzotriazole, 2-[2'-hydroxy-4'-(2"-ethylheptyl)oxyphenyl]benzotriazole, 2-[2'-hydroxy-4'-(2"-ethyloctyl)oxyphenyl]benzotriazole, 2-[2'-hydroxy-4'-(2"-propyloctyl)oxyphenyl]benzotriazole, 2-[2'-hydroxy-4'-(2"-propylheptyl)oxyphenyl]benzotriazole, 2-[2'-hydroxy-4'-(2"-propylhexyl)oxyphenyl]benzotriazole, 2-[2'-hydroxy-4'-(1"-ethylhexyl)oxyphenyl]benzotriazole, 2-[2'-hydroxy-4'-(1"-ethylheptyl)oxyphenyl]benzotriazole, 2-[2'-hydroxy-4'-(1"-ethyloctyl)oxyphenyl]benzotriazole, 2-[2'-hydroxy-4'-(1"-propyloctyl)oxyphenyl]benzotriazole, 2-[2'-hydroxy-4'-(2"-propylheptyl)oxyphenyl]benzotriazole, 2-[2'-hydroxy-4'-(2"-propylhexyl)oxyphenyl]benzotriazole, 2,2'-methylenebis[4-(1,1,3,3-tetramethylbutyl)-6-(2H-benzotriazole-2-yl)phenol, and a condensate of polyethyleneglycol and methyl-3-(3-tert-butyl-5-(2H-benzotriazole-2-yl)-4-hydroxyphenyl]propionate; a cyanoacrylate-based ultraviolet absorber such as 2'-ethylhexyl-2-cyano-3,3-diphenylacrylate, and ethyl-2-cyano-3,3-diphenylacrylate; a hindered amine-based ultraviolet absorber such as bis(2,2,6,6-tetramethyl-4-piperidyl)sebacate, succinic acid-bis(2,2,6,6-tetramethyl-4-piperidyl)ester, and 2-(3,5-di-tert-butyl)malonic acid-bis(1,2,2,6,6-pentamethyl-4-piperidyl)ester; and 1,8-dihydroxy-2-acetyl-3-methyl-6-methoxynaphthalene and its related compounds.

Examples of the fluorescent dye include 4,4'-bis[2-anilino-4-(hydroxyethyl)amino-1,3,5-triazinyl-6-amino]stilbene-2, 2'-disulfonic acid disodium salt, 4,4'-bis[2-anilino-4-bis(hydroxyethyl)amino-1,3,5-triazinyl-6-amino]stilbene-2,2'-disulfonic acid disodium salt, 4,4'-bis[2-methoxy-4-(hydroxyethyl)amino-1,3,5-triazinyl-6-amino]stilbene-2,2'-disulfonic acid disodium salt, 4,4'-bis[2-anilino-4-(hydroxypropyl)amino-1,3,5-triazinyl-6-amino]stilbene-2, 2'-disulfonic acid disodium salt, 4,4'-bis[2-m-sulfoanilino-4-bis(hydroxyethyl)amino-1,3,5-triazinyl-6-amino]stilbene-2, 2'-disulfonic acid disodium salt, 4-[2-p-sulfoanilino-4-bis (hydroxyethyl)amino-1,3,5-triazinyl-1-6-amino]-4'-[2-m-sulfoanilino-4-bis(hydroxyethyl)amino-1,3,5-triazinyl-6-amino]stilbene-2,2'-disulfonic acid tetrasodium salt, 4,4'-bis [2-p-sulfoanilino-4-bis(hydroxyethyl)amino-1,3,5-triazinyl-6-amino]stilbene-2,2'-disulfonic acid tetrasodium salt, 4,4'-bis[2-(2,5-disulfoanilino)-4-phenoxyamino-1,3,5-triazinyl-6-amino]stilbene-2,2'-disulfonic acid hexasodium salt, 4,4'-bis[2-(2,5-disulfoanilino)-4-(p-methoxycarbonylphenoxy) amino-1,3,5-triazinyl-6-amino]stilbene-2,2'-disulfonic acid hexasodium salt, 4,4'-bis[2-(p-sulfophenoxy)-4-bis(hydroxyethyl)amino-1,3,5-triazinyl-6-amino]stilbene-2,2'-disulfonic acid hexasodium salt, 4,4'-bis[2-(2,5-disulfoanilino)-4-formalinylamino-1,3,5-tri azinyl-6-amino]stilbene-2,2'-disulfonic acid hexasodium salt, and 4,4'-bis[2-(2,5-disulfoanilino)-4-bis(hydroxyethyl)amino-1,3,5-triazinyl-6-amino]stilbene-2,2'-disulfonic acid hexasodium salt.

When a color-developing composition of the present invention is used for a pressure sensitive copying paper, production of the pressure sensitive copying paper can be carried out similarly to when a known image storage stabilizer, color-developing agent or sensitizer is used. For example, a color forming compound that is formed into microcapsules by a known method is dispersed using an appropriate dispersant and applied onto a paper to prepare a color former sheet. Also, a dispersant solution of a color-developing agent is applied onto a paper to prepare a color-developing agent sheet. In doing so, when a color-developing composition of the present invention is used as an image storage stabilizer, it may be used by being dispersed into the dispersion solution of either one of the color former sheet and the color-developing agent sheet. A pressure sensitive copying paper is prepared by combining the both sheets thus prepared. The pressure sensitive copying paper may either be a unit or a so-called self content paper. Here, the unit consists of the upper paper which is coated with and carrying the microcapsules encapsulating an organic solvent solution of a color forming compound on the under surface, and the lower paper which is coated with and carrying a color-developing agent (an acid substance) on the upper surface. The self content paper is a paper that is coated with the microcapsules and the color-developing agent on the same surface of a paper.

EXAMPLES

The present invention is explained more specifically below with reference to the Examples, while the technical scope of the present invention shall not be limited to these exemplifications.

Abbreviations in the Examples means as follows.
4,4'-BPS: 4,4' dihydroxydiphenylsulfone
DCEE: bis(2-chloroethyl)ether Synthesis of a Color-developing Composition

Example 1

To a 1 L four-neck recovery flask equipped with an agitator and a thermometer, water (29.0 g) and 16.0 g (0.40 mol) of NaOH were added and dissolved at 90° C. Thereto, 50.0 g (0.20 mol) of 4,4'-BPS was added. The resultant solution was heated to 110° C. and added dropwise with 12.7 g (0.09 mol) of DCEE. Upon completion of the dropwise addition, the solution was kept at 110° C. and subjected to a condensation reaction for 6 hours. Upon completion of the reaction, 400.0 g of water was added to the reaction solution which was then kept at room temperature and adjusted for pH by the addition of 164.0 g of 5% HCl. After adjusting the pH, 60 mL of MeOH was added to the reaction solution which was then refluxed for 1 hour at 90° C. and allowed to cool. A crystal was separated by filtration and dried under reduced pressure at 70° C. to obtain the yield of 38.2 g. The result of the high-performance liquid chromatography analysis conducted far this crystal is shown in Table 1. In the table, the quantitative analysis values for 4,4'-BPS were obtained by an absolute calibration method and those values for other compounds were obtained by an internal reference method. The same procedure was followed to obtain the analytical results in the subsequent Examples.

Example 2

To a 1 L four-neck recovery flask equipped with an agitator and a thermometer, water (89.1 g) and 16.0 g (0.40 mol) of NaOH were added and dissolved at 90° C. Thereto, 50.0 g (0.20 mol) of 4,4'-BPS was added. The resultant solution was heated to 110° C. and added dropwise with 12.7 g (0.09 mol) of DCEE. Upon completion of the dropwise addition, the solution was kept at 110° C. and subjected to a condensation reaction for 6 hours. Upon completion of the reaction, 400.0 g of water was added to the reaction solution which was then kept at room temperature and adjusted for pH by the addition of 69.0 g of 5% HCl. After adjusting the pH, 20 mL of MeOH was added to the reaction solution which was then refluxed for 1 hour at 90° C. and allowed to cool. A crystal was separated by filtration and dried under reduced pressure at 70° C. to obtain the yield of 38.2 g. The result of the high-performance liquid chromatography analysis conducted for this crystal is shown in Table 1.

Example 3

To a 1 L four-neck recovery flask equipped with an agitator and a thermometer, water (89.1 g) and 16.0 g (0.40 mol) of NaOH were added and dissolved at 90° C. Thereto, 50.0 g (0.20 mol) of 4,4'-BPS was added. The resultant solution was heated to 110° C. and added dropwise with 12.7 g (0.09 mol) of DCEE. Upon completion of the dropwise addition, the solution was kept at 110° C. and subjected to a condensation reaction for 6 hours. Upon completion of the reaction, 400.0 g of water was added to the reaction solution which was then kept at room temperature and adjusted for pH by the addition of 69.0 g of 5% HCl. After adjusting the pH, 40 mL of MeOH was added to the reaction solution which was then refluxed for 1 hour at 90° C. and allowed to cool. A crystal was separated by filtration and dried under reduced pressure at 70° C. to obtain the yield of 38.2 g. The result of the high-performance liquid chromatography analysis conducted for this crystal is shown in Table 1.

Example 4

To a 1 L four-neck recovery flask equipped with an agitator and a thermometer, water (89.1 g) and 16.0 g (0.40 mol) of NaOH were added and dissolved at 90° C. Thereto, 50.0 g (0.20 mol) of 4,4'-BPS was added. The resultant solution was heated to 110° C. and added dropwise with 7.2 g (0.05 mol) of DCEE. Upon completion of the dropwise addition, the solution was kept at 110° C. and subjected to a condensation reaction for 6 hours. Upon completion of the reaction, 440.0 g of water was added to the reaction solution which was then kept at room temperature and adjusted for pH by the addition of 65.0 g of 5% HCl. After adjusting the pH, 200 mL of MeOH was added to the reaction solution which was then refluxed for 3 hours at 90° C. and allowed to cool. A crystal was separated by filtration and dried under reduced pressure at 70° C. to obtain the yield of 21.2 g. The result of the high-performance liquid chromatography analysis conducted for this crystal is shown in Table 1.

Example 5

To a 1 L four-neck recovery flask equipped with an agitator and a thermometer, water (89.1 g) and 16.0 g (0.40 mol) of NaOH were added and dissolved at 90° C. Thereto, 50.0 g (0.20 mol) of 4,4'-BPS was added. The resultant solution was heated to 110° C. and added dropwise with 15.7 g (0.11 mol) of DCEE. Upon completion of the dropwise addition, the solution was kept at 110° C. and subjected to a condensation reaction for 13 hours. Upon completion of the reaction, 440.0 g of water was added to the reaction solution which was then kept at room temperature and adjusted for pH by the addition of 5% HCl. After adjusting the pH, 300 mL of MeOH was added to the reaction solution which was then refluxed for 1 hour at 90° C. and allowed to cool. A crystal was separated by filtration and dried under reduced pressure at 70° C. to obtain the yield of 40.2 g. The result of the high-performance liquid chromatography analysis conducted for this crystal is shown in Table 1.

Comparative Example 1

To a 1 L four-neck recovery flask equipped with an agitator and a thermometer, water (29.0 g) and 16.0 g (0.40 mol) of NaOH were added and dissolved at 90° C. Thereto, 50.0 g (0.20 mol) of 4,4'-BPS was added. The resultant solution was heated to 110° C. and added dropwise with 12.7 g (0.09 mol) of DCEE. Upon completion of the dropwise addition, the solution was kept at 110° C. and subjected to a condensation reaction for 6 hours. Upon completion of the reaction, 400.0 g of water was added to the reaction solution which was then kept at room temperature and adjusted for pH by the addition of 164.0 g of 5% HCl. After adjusting the pH, the reaction solution was refluxed for 1 hour at 90° C. and allowed to cool. A crystal was separated by filtration and dried under reduced pressure at 70° C. to obtain the yield of 39.3 g. The result of the high-performance liquid chromatography analysis conducted for this crystal is shown in Table 1.

Comparative Example 2

To a 1 L four-neck recovery flask equipped with an agitator and a thermometer, water (89.1 g) and 16.0 g (0.40 mol) of NaOH were added and dissolved at 90° C. Thereto, 50.0 g (0.20 mol) of 4,4'-BPS was added. The resultant solution was heated to 110° C. and added dropwise with 7.2 g (0.05 mol) of DCEE. Upon completion of the dropwise addition, the solution was kept at 110° C. and subjected to a condensation reaction for 6 hours. Upon completion of the reaction, 440.0 g of water was added to the reaction solution which was then kept at room temperature and adjusted for pH by the addition of 65.0 g of 5% HCl. After adjusting the pH, the reaction solution was refluxed for 3 hours at 90° C. and allowed to cool. A crystal was separated, by filtration and dried under reduced pressure at 70° C. to obtain the yield of 23.3 g. The result of the high-performance liquid chromatography analysis conducted for this crystal is shown in Table 1.

Comparative Example 3

To a 1 L four-neck recovery flask equipped with an agitator and a thermometer, water (89.1 g) and 16.0 g (0.40 mol) of NaOH were added and dissolved at 90° C. Thereto, 50.0 g (0.20 mol) of 4,4'-BPS was added. The resultant solution was heated to 110° C. and added dropwise with 15.7 g (0.11 mol) of DCEE. Upon completion of the dropwise addition, the solution was kept at 110° C. and subjected to a condensation reaction for 8 hours. Upon completion of the reaction, 440.0 g of water was added to the reaction solution which was then kept at room temperature and adjusted for pH by the addition of 5% HCl. After adjusting the pH, the reaction solution was refluxed for 1 hour at 90° C. and allowed to cool. A crystal was separated by filtration and dried under reduced pressure at 70° C. to obtain the yield of 42.2 g. The result of the high-performance liquid chromatography analysis conducted for this crystal is shown in Table 1.

TABLE 1

| | Raw material | | Solvent | Product (wt %) | | | | |
|---|---|---|---|---|---|---|---|---|
| | 4,4'-BPS (mol) | DCEE (mol) | Methanol (ml) | 4,4'-BPS | $n = 1$ compound | $n = 2$ compound | $n = 3$ compound | $n = 4$-6 compound |
| Examples | | | | | | | | |
| 1 | 0.20 | 0.09 | 60 | 0.8 | 37.2 | 19.3 | 8.9 | 7.5 |
| 2 | 0.20 | 0.09 | 20 | 0.8 | 38.2 | 19.9 | 9.1 | 8.3 |
| 3 | 0.20 | 0.09 | 40 | 0.8 | 36.9 | 19.9 | 9.3 | 8.5 |
| 4 | 0.20 | 0.05 | 200 | 1.0 | 56.6 | 20.1 | 6.5 | 3.0 |
| 5 | 0.20 | 0.11 | 300 | 0.7 | 25.2 | 13.8 | 8.1 | 8.9 |
| Comparative Examples | | | | | | | | |
| 1 | 0.20 | 0.09 | — | 4.4 | 35.2 | 19.3 | 9.4 | 8.1 |
| 2 | 0.20 | 0.05 | — | 2.7 | 58.0 | 19.2 | 5.8 | 2.5 |
| 3 | 0.20 | 0.11 | — | 3.1 | 27.2 | 15.3 | 9.0 | 8.4 |

Note 1)
In the table, $n = 1$ to $n = 6$ compounds represent those compounds wherein n in the formula below is 1 to 6.

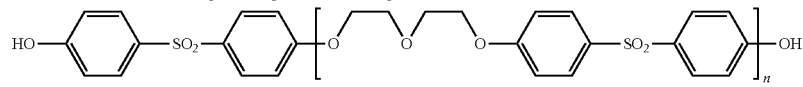

Note 2)
Numerical values for the products indicate wt % of each component in the total amount of the products.

TEST EXAMPLES

Test Example 1

Powder X-ray Diffraction

Figure 2:
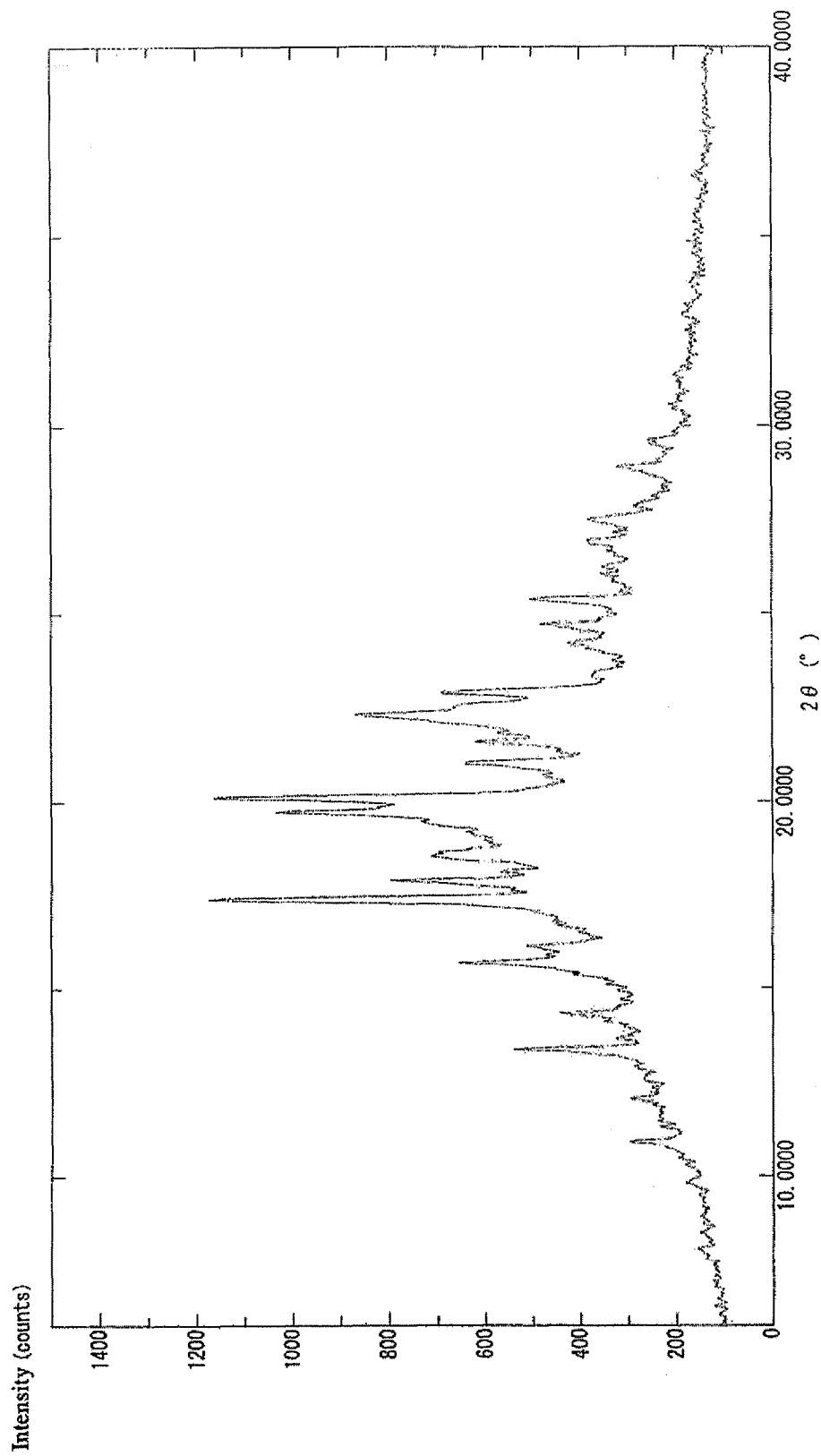
FIG. 2 shows the result of X-ray diffraction carried out for the reaction composition of Example 2 of the present invention.
Figure 3:
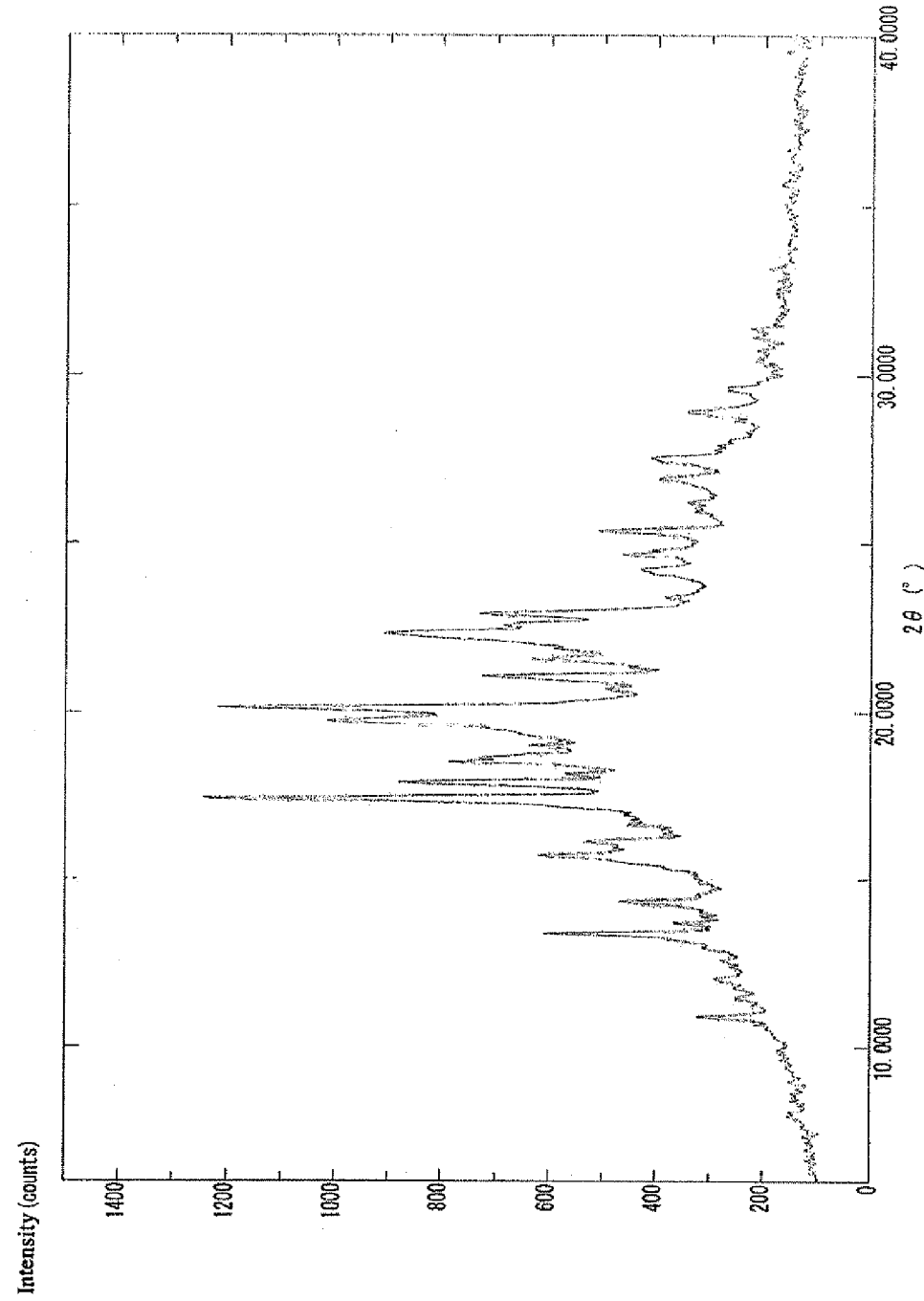
FIG. 3 shows the result of X-ray diffraction carried out for the reaction composition of Example 3 of the present invention.
Figure 4:
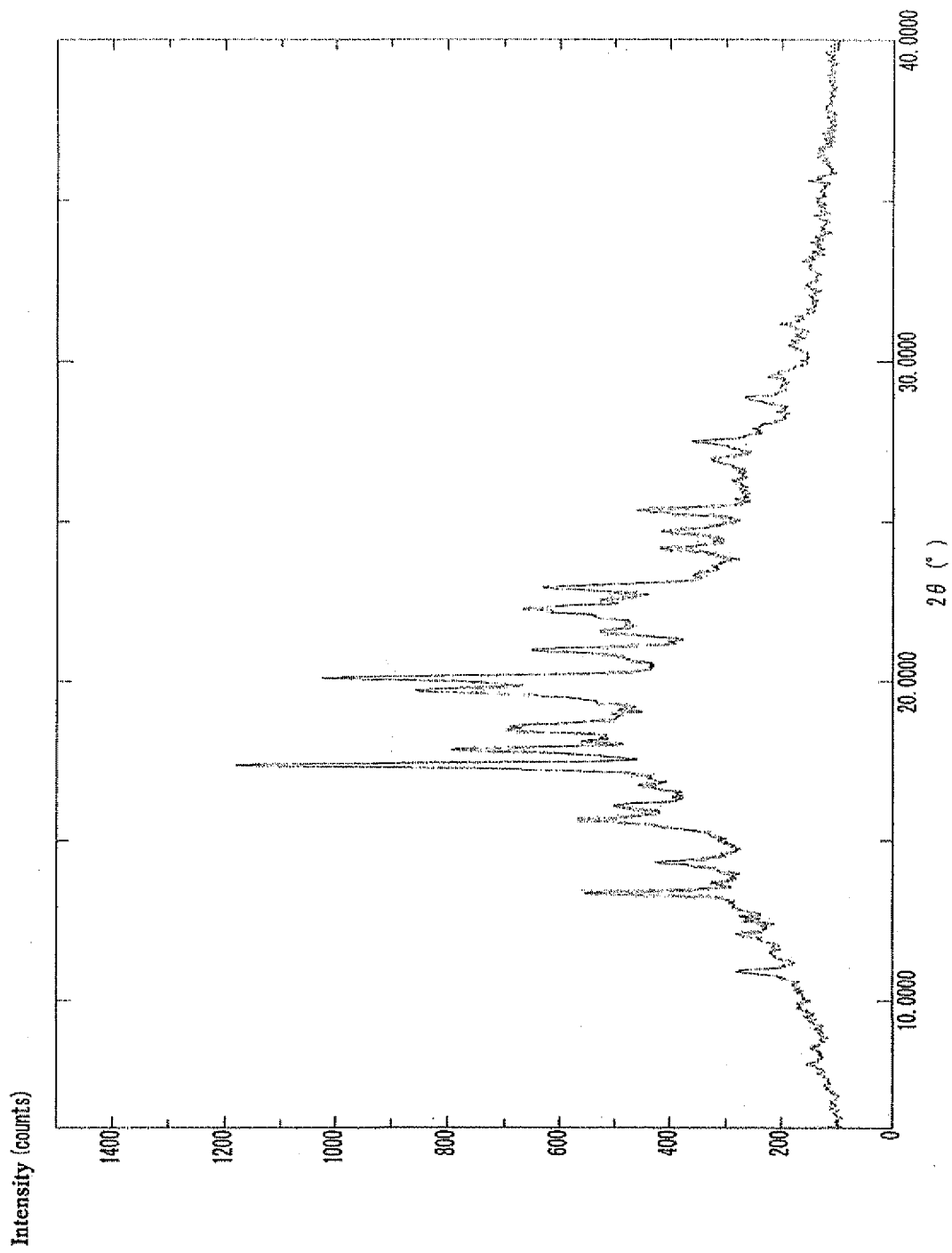
FIG. 4 shows the result of X-ray diffraction carried out for the reaction composition of Example 4 of the present invention.
Figure 5:
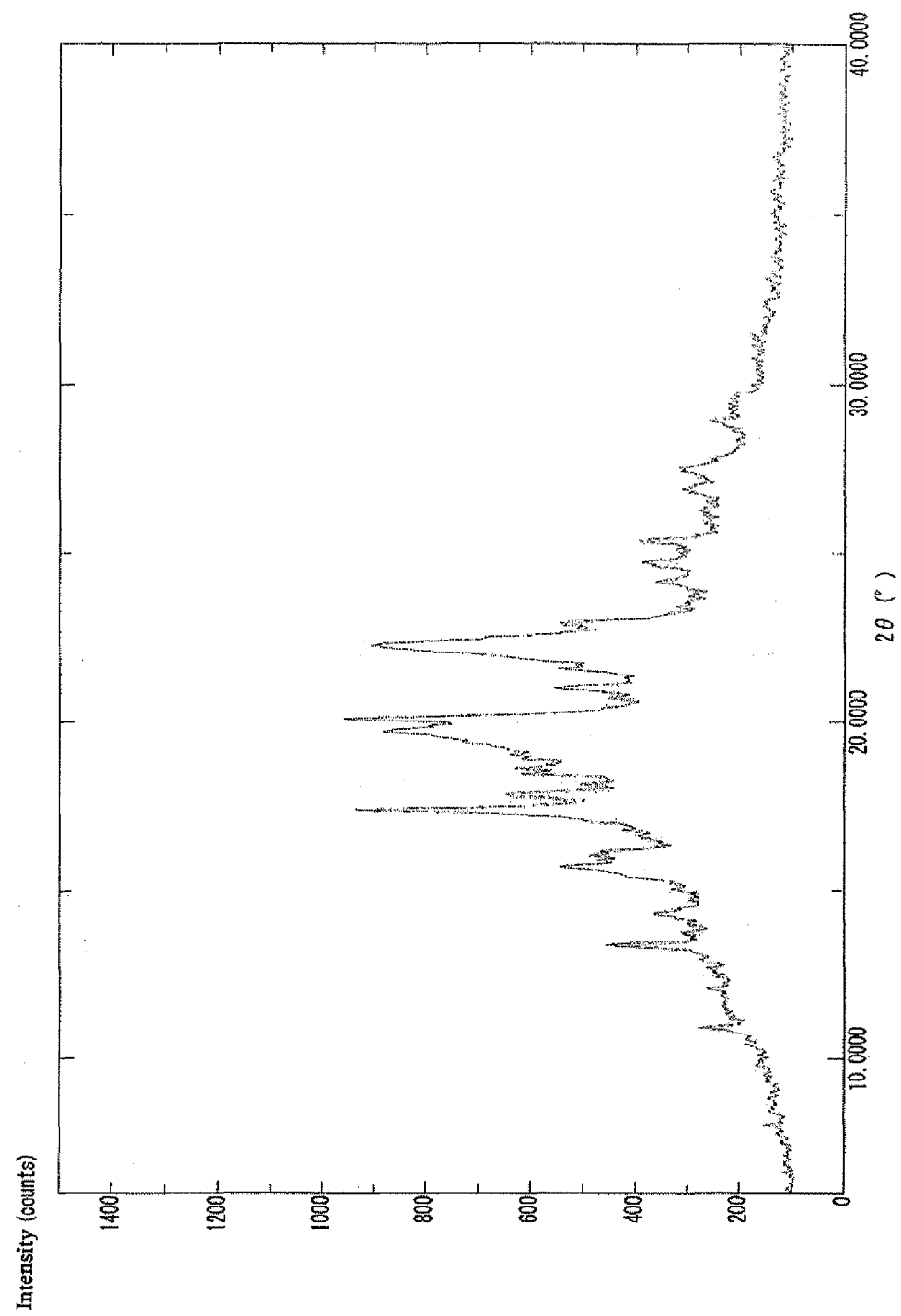
FIG. 5 shows the result of X-ray diffraction carried out for the reaction composition of Example 5 of the present invention.
Figure 6:
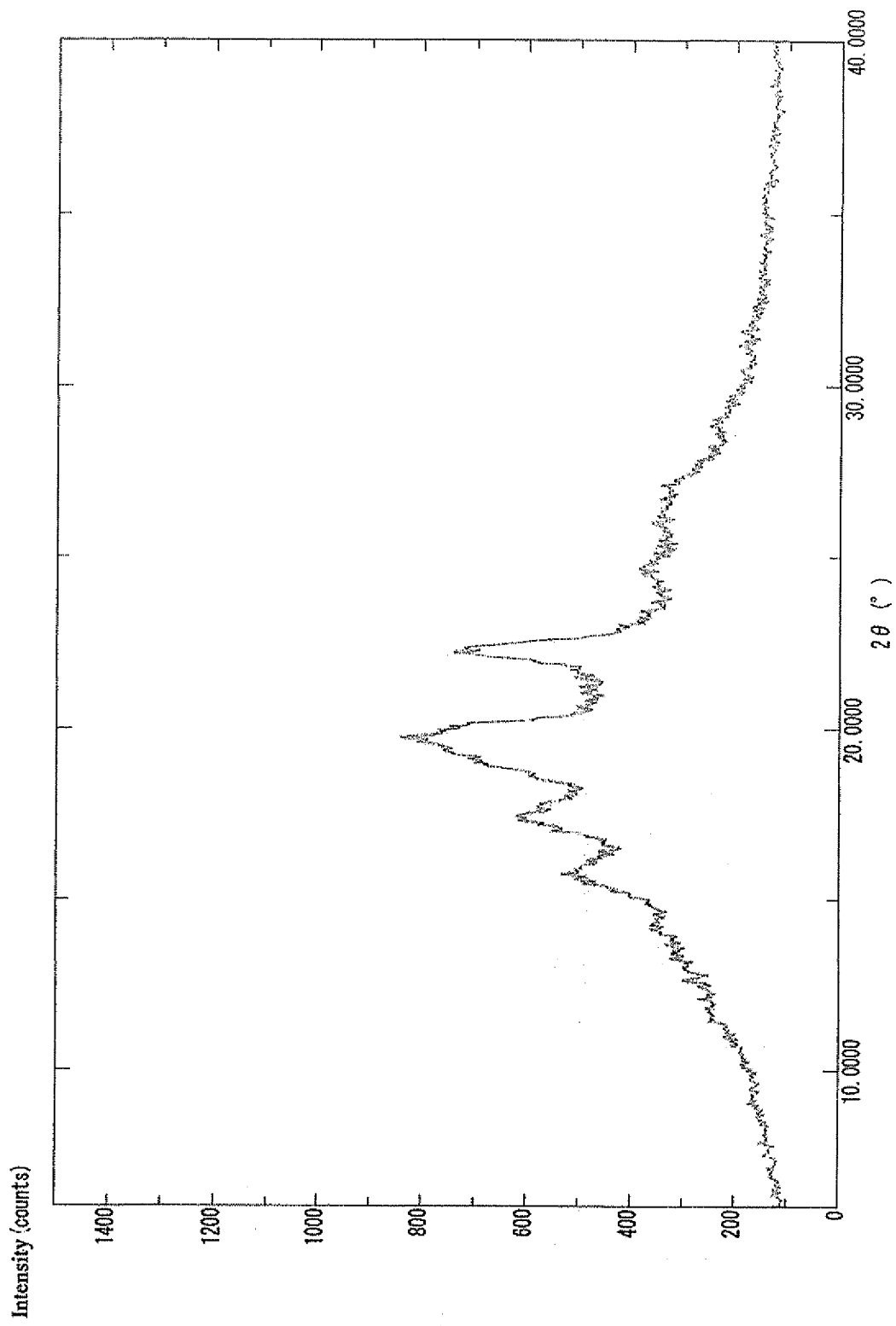
FIG. 6 shows the result of X-ray diffraction carried out for the reaction composition of Comparative Example 1 of the present invention.
Figure 7:
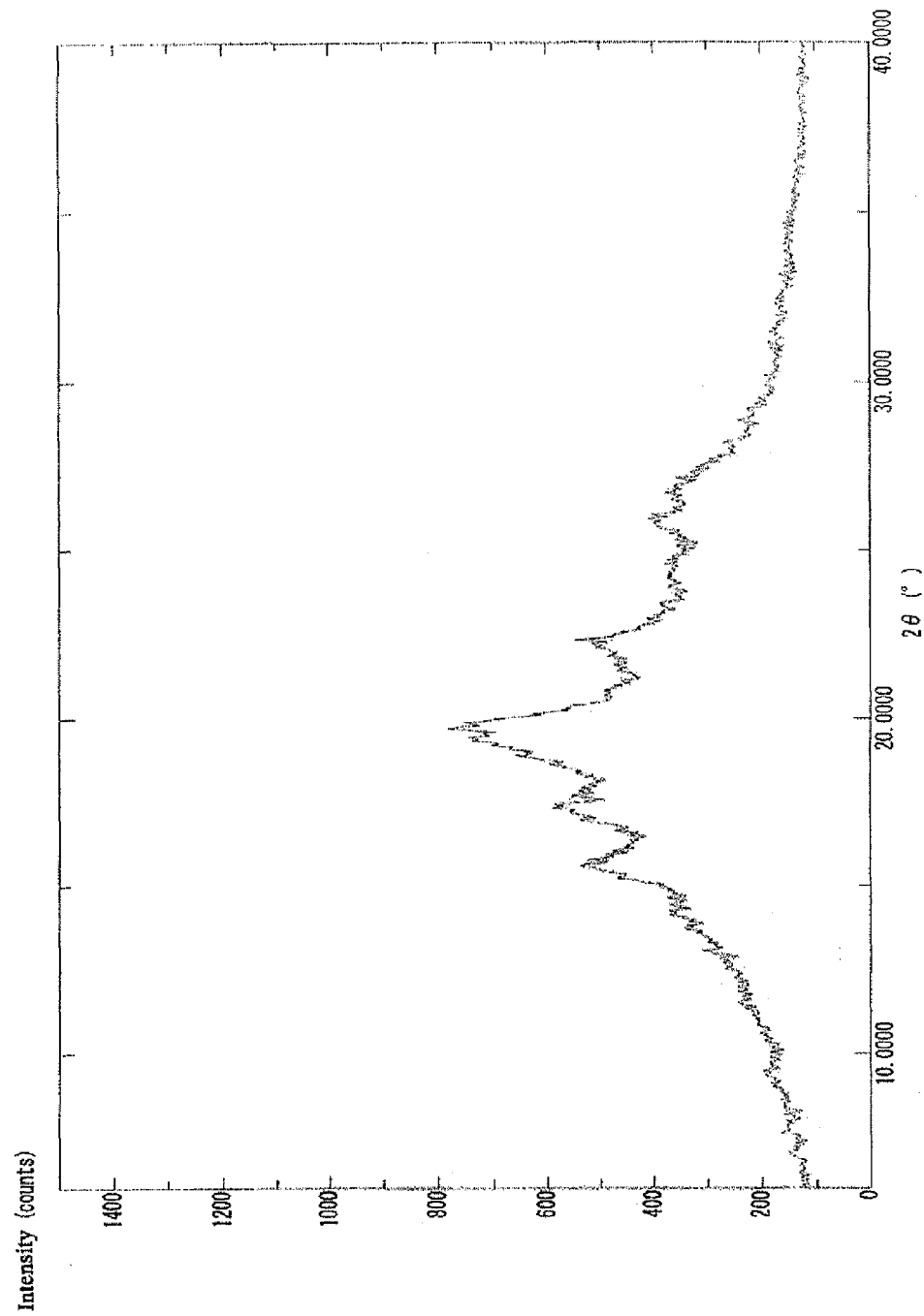
FIG. 7 shows the result of X-ray diffraction carried out for the reaction composition of Comparative Example 2 of the present invention.
Figure 8:
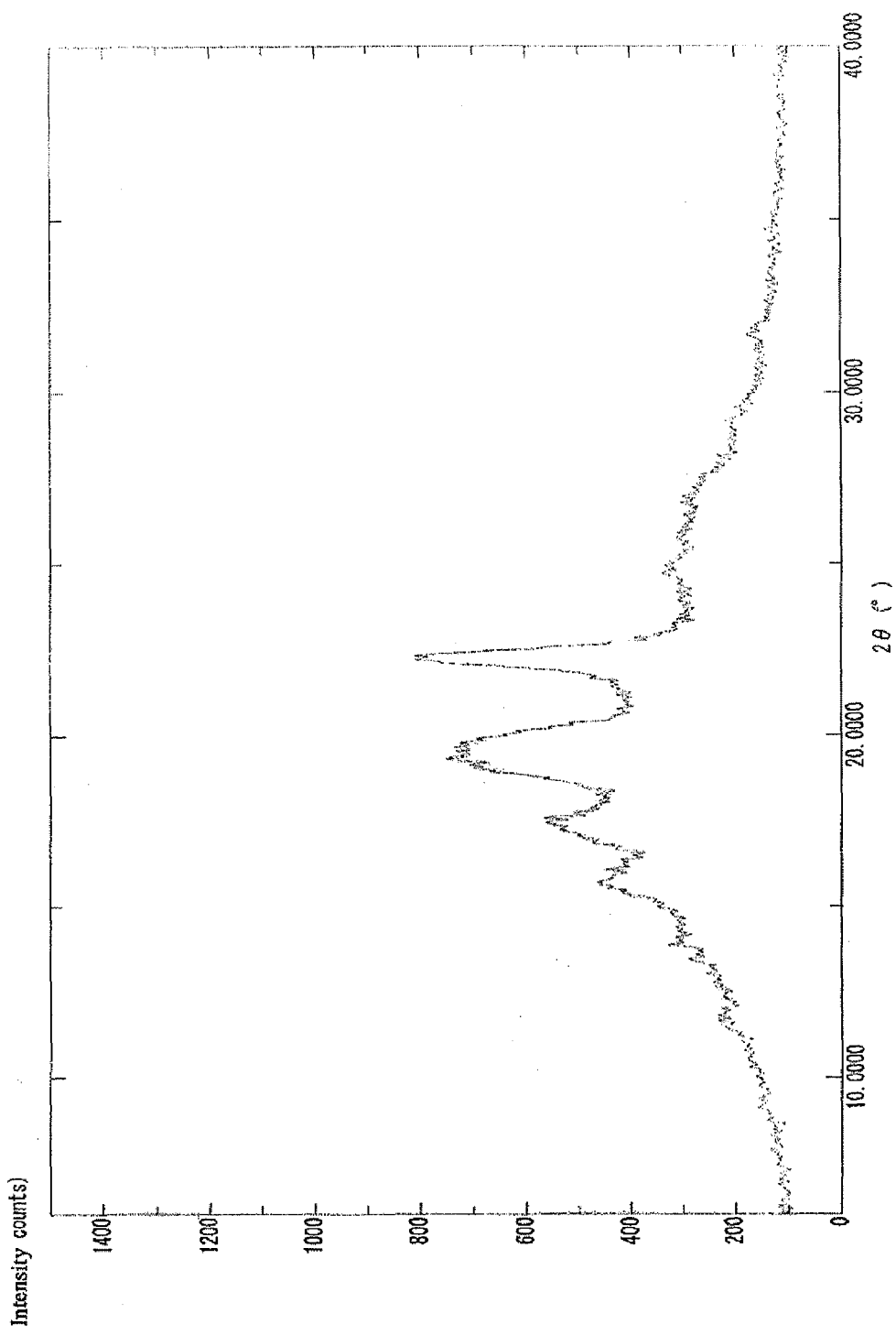
FIG. 8 shows the result of X-ray diffraction carried out for the reaction composition of Comparative Example 3 of the present invention.

Examples 1 to 5 and Comparative Examples 1 to 3 were respectively analyzed using a X-ray diffraction device, Ultima IV (Rigaku). The results are shown in FIGS. 1 to 8.

Test Example 2

Assessment of Crystallinity

Peaks were separated by a multiple peak method based on the results of the powder X-ray measurement in Test Example 1. The entire area was calculated from all the separated peaks, and the total of the major peak areas derived from a high crystalline n=1 compound (being crystalline) was calculated. Then a content area ratio which serves as an index for assessing the high crystallinity (being crystalline) was calculated. The values were calculated according to the following formula. The major peaks refer to the 11 peaks in total: $2\theta=13.3$, 14.3, 17.4, 17.9, 19.7, 20.1, 21.1, 22.9, 25.4, 27.5 and 28.9.

These were recognized as a peak only when the half-value breadth was 0.4 or less. The results are collectively shown in the following Table 2.

Area ratio of the major peaks=Area of the major peaks/Area of all the peaks

Further, a calibration curve was prepared based on the area ratio of the major peaks when the high crystalline n=1 compound occupied 100% and the mass ratio from the HPLC. Then, the content ratio of a high crystalline n=1 compound (content ratio of the crystalline material) among entire n=1 compound was calculated from the area ratio of the major peaks of the samples. The results are shown in Table 2.
* Specimens for preparing the calibration curve were prepared by carrying out reactions under the conditions similar to each Example and then removing only n=1 compound, and subsequently adding thereto the n=1 compound (crystalline ratio of 100%) that had been newly synthesized separately.

TABLE 2

|  | HPLC [wt %] | A [area %] | B [area %] | A/B [wt %] |
|---|---|---|---|---|
| Example 1 | 37.2 | 13.6 | 13.9 | 98 |
| Example 2 | 38.2 | 11.2 | 14.4 | 78 |
| Example 3 | 36.9 | 12.5 | 13.8 | 91 |
| Example 4 | 56.6 | 9.0 | 21.3 | 42 |
| Example 5 | 25.2 | 7.0 | 12.3 | 57 |
| Comparative Ex. 1 | 36.4 | 0 |  | 0 |
| Comparative Ex. 2 | 55.9 | 0 |  | 0 |
| Comparative Ex. 3 | 26.3 | 0 |  | 0 |

HPLC: wt % of n = 1 compound in the total amount of the product, as obtained by the liquid chromatography.
A: The area ratio of the major peaks of the high crystalline n = 1 compound = A
B: The area ratio of the major peaks when the high crystalline n = 1 compound occupied 100% = B
A/B: The content ratio of the high crystalline n = 1 among entire n = 1 in a sample.

Example of Production of a Thermal Recording Paper

Example 6

Dispersion solution of dye (solution A)

| 3-di-n-butylamino-6-methyl-7-anilinofluoran | 16 parts |
|---|---|
| Aqueous solution of 10% polyvinylalcohol | 84 parts |

Dispersion solution of color-developing agent (solution B)

| Reaction composition of Example 1 | 16 parts |
|---|---|
| Aqueous solution of 10% polyvinylalcohol | 84 parts |

Dispersion solution of loading material (solution C)

| Calcium carbonate | 27.8 parts |
|---|---|
| Aqueous solution of 10% polyvinylalcohol | 26.2 parts |
| Water | 71 parts |

First, the mixture of each of the solutions A to C consisting of respective compositional parts were respectively ground well with a sand grinder and the dispersion solutions of solutions A to C with respective components were prepared. An application solution was prepared by mixing 1 part by mass of solution A, 2 parts by mass of solution B and 4 parts by mass of solution C. This application solution was applied onto a white paper using a wire rod (Webster, Wire bar No. 12) and the paper was dried. The paper was then subjected to a calendar treatment to prepare a thermal recording paper (application solution was used at about 5.5 g/m$^2$ as dried mass).

Comparative Example 4

A thermal recording paper was produced by the method described in Example 6, except that the reaction composition of Comparative Example 1 was used instead of the reaction composition of Example 1 in the dispersion solution of color-developing agent (solution B) in Example 6.

Examples 7-10 and Comparative Examples 5 and 6

A thermal recording paper was produced by the method described in Example 6, except that the reaction compositions of Examples 2 to 5 and the reaction compositions of Comparative Examples 2 and 3 were used in the dispersion solution of color-developing agent (solution B) in Example 6.

Test Example

Assessment of Thermal Recording Paper—Background Heat Resistance Test

A part of the thermal recording papers respectively prepared in Examples 6 to 10 and Comparative Examples 4 to 6 was cut off and kept in a thermostat device (YAMATO, Product name: DK-400) for 24 hours at 80° C., 90° C. and 100° C., and the background density (Macbeth value) of each test paper was measured. Table 3 collectively shows the results.

TABLE 3

|  | Color-developing composition | Assessment of thermal recording paper (Background heat resistance test) | | |
|---|---|---|---|---|
|  |  | 80° C. | 90° C. | 100° C. |
| Examples | | | | |
| 6 | Reaction composition of Example 1 | 0.12 | 0.22 | 0.38 |
| 7 | Reaction composition of Example 2 | 0.12 | 0.25 | 0.45 |
| 8 | Reaction composition of Example 3 | 0.11 | 0.23 | 0.41 |
| 9 | Reaction composition of Example 4 | 0.14 | 0.37 | 0.52 |
| 10 | Reaction composition of Example 5 | 0.11 | 0.16 | 0.25 |
| Comparative Examples | | | | |
| 4 | Reaction composition of Comparative Example 1 | 0.18 | 0.43 | 0.65 |
| 5 | Reaction composition of Comparative Example 2 | 0.26 | 0.69 | 0.91 |
| 6 | Reaction composition of Comparative Example 3 | 0.26 | 0.41 | 0.62 |

Example 11

Dispersion solution of dye (solution A)

| | |
|---|---|
| 3-di-n-butylamino-6-methyl-7-anilinofluoran | 16 parts |
| Aqueous solution of 10% polyvinylalcohol | 84 parts |

Dispersion solution of color-developing agent (solution B)

| | |
|---|---|
| Reaction composition of Example 1 | 16 parts |
| Aqueous solution of 10% polyvinylalcohol | 84 parts |

Dispersion solution of color-developing adjuvant (solution D)

| | |
|---|---|
| 4-{[4-(1-methylethoxy)phenyl]sulfonyl}phenol | 16 parts |
| Aqueous solution of 10% polyvinylalcohol | 84 parts |

Dispersion solution of loading material (solution C)

| | |
|---|---|
| Calcium carbonate | 27.8 parts |
| Aqueous solution of 10% polyvinylalcohol | 26.2 parts |
| Water | 71 parts |

First, the mixture of each of the solutions A, B and D consisting of respective compositional parts were respectively ground well with a sand grinder and the dispersion solutions of solutions A, B and D with respective components were prepared. An application solution was prepared by mixing 1 part by mass of solution A, 1 part by mass of solution B, 1 part by mass of solution D, and 4 parts by mass of solution C. This application solution was applied to a white paper using a wire rod (Webster, Wire bar No. 12) and the paper was dried. The paper was then subjected to a calendar treatment to prepare a thermal recording paper (application solution was used at about 5.5 g/m² as dried mass).

Example 12

A thermal recording paper was produced by the method described in Example 11, except that 4-{[4-(propoxy)phenyl]sulfonyl}phenol was used instead of 4-{[4-(1-methylethoxy)phenyl]sulfonyl}phenol in the dispersion solution of color-developing adjuvant (solution D) in Example 11.

Example 13

A thermal recording paper was produced by the method described in Example 11, except that 2-(4-hydroxyphenylsulfonyl) phenol was used instead of 4-{[4-(1-methylethoxy)phenyl]sulfonyl}phenol in the dispersion solution of color-developing adjuvant (solution D) in Example 11.

Example 14

A thermal recording paper was produced by the method described in Example 11, except that 4-{[4-(allyloxy)phenyl]sulfonyl}phenol was used instead of 4-{[4-(1-methylethoxy)phenyl]sulfonyl}phenol in the dispersion solution of color-developing adjuvant (solution D) in Example 11.

Comparative Example 7

A thermal recording paper was produced by the method described in Example 11, except that the reaction composition of Comparative Example 1 was used instead of the reaction composition of Example 1 in the dispersion solution of color-developing agent (solution B) in Example 11.

Comparative Example 8

A thermal recording paper was produced by the method described in Example 12, except that the reaction composition of Comparative Example 1 was used instead of the reaction composition of Example 1 in the dispersion solution of color-developing agent (solution B) in Example 12.

Comparative Example 9

A thermal recording paper was produced by the method described in Example 13, except that the reaction composition of Comparative Example 1 was used instead of the reaction composition of Example 1 in the dispersion solution of color-developing agent (solution B) in Example 13.

Comparative Example 10

A thermal recording paper was produced by the method described in Example 14, except that the reaction composition of Comparative Example 1 was used instead of the reaction composition of Example 1 in the dispersion solution of color-developing agent (solution B) in Example 14.

Test Example

Assessment of Thermal Recording Paper—Background Heat Resistance Test

A part of the thermal recording papers respectively produced in Examples 11 to 14 and Comparative Examples 7 to 10 was cut off and kept in a thermostat device (YAMATO, Product name: DK-400) for 24 hours at 80° C. and 90° C., and the background density (Macbeth value) of each test paper was measured. Table 4 collectively shows the results.

TABLE 4

| | Assessment of thermal recording paper (Background heat resistance test) | |
|---|---|---|
| | 80° C. | 90° C. |
| Examples | | |
| 11 | 0.25 | 0.58 |
| 12 | 0.13 | 0.19 |
| 13 | 0.15 | 0.24 |
| 14 | 0.11 | 0.18 |
| Comparative Examples | | |
| 7 | 0.44 | 0.84 |
| 8 | 0.22 | 0.38 |
| 9 | 0.18 | 0.38 |
| 10 | 0.18 | 0.30 |

INDUSTRIAL APPLICABILITY

The present invention enables provision of a recording material which has a superior heat resistance on the background part, as well as enabling reduction of the content of a dihydroxydiphenylsulfone derivative, such 4,4'-dihydroxydiphenylsulfone, in a color-developing composition to 2% by mass or less or even to 1% by mass or less.

The invention claimed is:

1. A color-developing composition which is a reaction composition containing a mixture of compounds represented by formula (III)

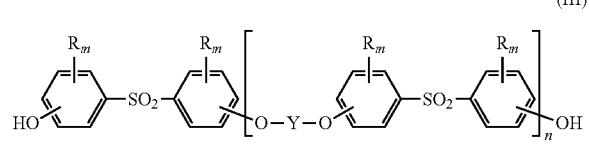

(wherein R, Y and m have the same meaning as defined below and n represents an integer of 1 to 6) that are obtained by reacting a dihydroxydiphenylsulfone derivative represented by formula (I)

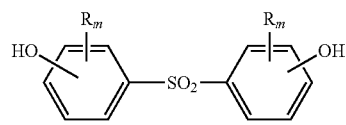

(wherein each R independently represents a halogen atom, C1-C6 alkyl group or C2-C6 alkenyl group, and m represents an integer of 0 to 4) with a dihalide represented by formula (II)

{wherein X represents a halogen atom, Y either represents a linear, branched or cyclic C1-C12 hydrocarbon group which may have an ether bond or represents the following formula

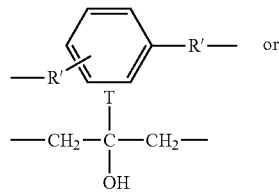

(wherein R' represents a methylene group or ethylene group, and T represents a hydrogen atom or C1-C4 alkyl group)}, wherein the content of a n=1 compound in the reaction composition is 5-80% by mass relative to the solid content in the whole composition and wherein 10% by mass or more of the n=1 compound is a crystalline material.

2. The color-developing composition according to claim 1, wherein the compound represented by formula (I) is 4,4'-dihydroxydiphenylsulfone, the dihalide represented by formula (II) is bis(2-chloroethyl)ether, and the n=1 compound of formula (III) which is in an amount of 5-80% by mass relative to the solid content of the whole reaction composition is 2,2'-bis[4-(4-hydroxyphenylsulfonyl)phenoxy]diethylether.

3. The color-developing composition according to claim 1 or 2, wherein the content of the dihydroxydiphenylsulfone derivative represented by formula (I) in the solid content of the reaction composition is 2% by mass or less.

4. A method for producing the color-developing composition according to claim 1 or 2, wherein the method comprises reacting the dihydroxydiphenylsulfone derivative represented by formula (I) with the dihalide represented by formula (II) in a solvent, mixing the reaction solution with an organic solvent, and separating a product by filtration.

5. A color-developing composition which is a reaction composition of 4,4'-dihydroxydiphenylsulfone and bis(2-chloroethyl)ether, wherein the content of 2,2'-bis[4-(4-hydroxyphenylsulfonyl)phenoxy]diethylether in the reaction composition is 5-80% by mass relative to the solid content in the whole composition and wherein the reaction composition has a peak at $2\theta=17.4$ in an X-ray diffraction.

6. The color-developing composition according to claim 5, which has peaks at $2\theta=13.3, 17.4, 18.4$ and $21.0$ in the X-ray diffraction.

7. The color-developing composition according to claim 5 or 6, wherein the content of 4,4'-dihydroxydiphenylsulfone in the solid content of the reaction composition is 2% by mass or less.

8. A method for producing the color-developing composition according to claim 5 or 6, wherein the method comprises reacting 4,4'-dihydroxydiphenylsulfone with bis(2-chloroethyl)ether in a solvent, mixing the reaction solution with an organic solvent, and separating a product by filtration.

9. A recording material comprising the color-developing composition of claim 1 or 5.

* * * * *